(12) United States Patent
Hofmann et al.

(10) Patent No.: US 12,233,056 B2
(45) Date of Patent: *Feb. 25, 2025

(54) LYSYL OXIDASE INHIBITORS FOR TREATING MYELOID MALIGNANCIES

(71) Applicant: Syntara Limited, Frenchs Forest (AU)

(72) Inventors: Wolf-Karsten Hofmann, Mannheim (DE); Daniel Nowak, Mannheim (DE); Vladimir Ryabov, Mannheim (DE); Qingyu Xu, Mannheim (DE); Eva Altrock, Vaihingen/Enz (DE)

(73) Assignee: Syntara Limited, Frenchs Forest (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/131,183

(22) Filed: Apr. 5, 2023

(65) Prior Publication Data

US 2023/0321075 A1   Oct. 12, 2023

(30) Foreign Application Priority Data

Apr. 6, 2022 (AU) ................................ 2022900904

(51) Int. Cl.
*A61K 31/47* (2006.01)
*A61K 31/706* (2006.01)
*A61P 35/00* (2006.01)
*A61P 35/02* (2006.01)

(52) U.S. Cl.
CPC ............ *A61K 31/47* (2013.01); *A61K 31/706* (2013.01); *A61P 35/00* (2018.01); *A61P 35/02* (2018.01)

(58) Field of Classification Search
CPC ....... A61K 31/47; A61K 31/706; A61P 35/02; A61P 35/00
See application file for complete search history.

(56) References Cited

U.S. PATENT DOCUMENTS

| | | | |
|---|---|---|---|
| 4,454,158 | A | 6/1984 | Bey |
| 4,699,928 | A | 10/1987 | McDonald |
| 4,943,593 | A | 7/1990 | Palfreyman et al. |
| 4,965,288 | A | 10/1990 | Palfreyman et al. |
| 5,021,456 | A | 6/1991 | Palfreyman et al. |
| 5,059,714 | A | 10/1991 | Palfreyman et al. |

(Continued)

FOREIGN PATENT DOCUMENTS

| | | |
|---|---|---|
| WO | 2003/097612 A1 | 11/2003 |
| WO | 2006/053555 A2 | 5/2006 |

(Continued)

OTHER PUBLICATIONS

Duarte D, Vale N. Evaluation of synergism in drug combinations and reference models for future orientations in oncology. Curr Res Pharmacol Drug Discov. May 12, 2022;3:100110. doi: 10.1016/j.crphar.2022.100110 (Year: 2022).*

(Continued)

*Primary Examiner* — Clinton A Brooks
*Assistant Examiner* — Jerica Katlynn Wilson
(74) *Attorney, Agent, or Firm* — Haley Guiliano LLP

(57) ABSTRACT

Lysyl oxidase (LOX) inhibitors, lysyl oxidase-like (LOXL) inhibitors, or pharmaceutically acceptable salts thereof and methods for the treatment of myeloid malignancies, comprising administering a therapeutically effective amount of those inhibitors alone or optionally in combination with a second therapeutic agent.

9 Claims, 6 Drawing Sheets

(56) References Cited

U.S. PATENT DOCUMENTS

| | | | |
|---|---|---|---|
| 5,182,297 | A | 1/1993 | Palfreyman et al. |
| 5,252,608 | A | 10/1993 | Palfreyman et al. |
| 2006/0004015 | A1 | 1/2006 | Schohe et al. |
| 2008/0293936 | A1 | 11/2008 | Burchardt |
| 2009/0053224 | A1 | 2/2009 | Smith et al. |
| 2021/0353571 | A1* | 11/2021 | Findlay .................. A61P 35/04 |
| 2023/0349907 | A1 | 11/2023 | Findlay et al. |

FOREIGN PATENT DOCUMENTS

| | | |
|---|---|---|
| WO | 2007/120528 A2 | 10/2007 |
| WO | 2011/090760 A1 | 7/2011 |
| WO | 2016/144702 A1 | 9/2016 |
| WO | 2016/144703 A1 | 9/2016 |
| WO | 2017/003862 A1 | 1/2017 |
| WO | 2017/015221 A1 | 1/2017 |
| WO | 2017/136870 A1 | 8/2017 |
| WO | 2017/136871 A1 | 8/2017 |
| WO | 2017/139274 A1 | 8/2017 |
| WO | 2017/141049 A1 | 8/2017 |
| WO | 2018/048930 A1 | 3/2018 |
| WO | 2018/157190 A1 | 9/2018 |
| WO | 2019/073251 A1 | 4/2019 |
| WO | 2019/234418 A1 | 12/2019 |
| WO | 2020/024017 A1 | 2/2020 |
| WO | 2020/099886 A1 | 5/2020 |
| WO | 2021/012014 A1 | 1/2021 |

OTHER PUBLICATIONS

Talleirda et al.Quantitative Methods for Assessing Drug Synergism. Genes and Cancer. 2012, 2(11), 1003-1008 (Year: 2012).*

Piasecki et al. Lysyl oxidase inhibition in primary myelofibrosis: A renewed strategy. Arch Stem Cell Ther. 2020, 1(1), 23-27 (Year: 2020).*

Mokhtari et al., Combination therapy in combating cancer. Oncotarget, 2017, 8 (23), 38022-38043 (Year: 2017).*

Ma et al.Comparison Between Decitabine and Azacitidine for Patients With Acute Myeloid Leukemia and Higher-Risk Myelodysplastic Syndrome: A Systematic Review and Network Meta-Analysis. Front. Pharmacol. 2021, 12, 701690 (Year: 2021).*

Ball et al. (Leuk Lymphoma. May 2017; 58(5): 1022-1036). (Year: 2017).*

Appelbaum, F. et al., Allogeneic bone marrow transplantation for myelodysplastic syndrome: outcomes analysis according to IPSS score, Leukemia, 12(1):S25-29 (1998).

Bessler, M. et al., Dyskeratosis congenita, FEBS Lett, 584, 3831-3838 (2020).

Cazzola, M. et al., Myelodysplastic Syndromes, New England Journal of Medicine, 383, 1358-1374 (2020).

Chen, W. et al., Lysyl oxidase (LOX) family members: rationale and their potential as therapeutic targets for liver fibrosis, Hepatology, 72:729-741 (2020).

Cutler, C. S. et al., A decision analysis of allogeneic bone marrow transplantation for the myelodysplastic syndromes: delayed transplantation for low-risk myelodysplasia is associated with improved outcome, Blood, 104, 579-585 (2004).

Damaj, G., et al., Impact of azacitidine before allogeneic stem-cell transplantation for myelodysplastic syndromes: a study by the Société Française de Greffe de Moelle et de Thérapie-Cellulaire and the Groupe-Francophone des Myélodysplasies, J. Clin. Oncol., 30:4533-4540 (2012).

Fenaux, P. et al., Efficacy of azacitidine compared with that of conventional care regimens in the treatment of higher-risk myelodysplastic syndromes: a randomised, open-label, phase III study, The Lancet Oncology, 10: 223-232 (2009).

Gary Philips, Clinical stage novel, small molecule medicines focused on cancer and fibrotic disease, Investor Presentation, Apr. 2021, 30 pages.

Greenberg, P. et al., International scoring system for evaluating prognosis in myelodysplastic syndromes, Blood, 89(6):2079-88 (1997).

Gueller, S. et al., Identification of defects in the transcriptional program during lineage-specific in vitro differentiation of CD34( +) cells selected from patients with both low- and high-risk myelodysplastic syndrome, Exp Hematol, 38:718-732, 732 e711-716 (2010).

Kee, Y. et al., Molecular pathogenesis and clinical management of Fanconi anemia, J. Clin. Invest., 122:3799-3806 (2012).

Ley, T. et al., Genomic and epigenomic landscapes of adult de novo acute myeloid leukemia, N. Engl. J. Med., 368(22):2059-74 (2013).

Ma, X, Epidemiology of myelodysplastic syndromes, Am. J. Med., 125 S2-5 (2012).

Martino, R. et al., Myelodysplastic Syndrome subcommittee of the Chronic Leukemia Working Party of the European, G. Marrow Transplantation, Retrospective comparison of reduced-intensity conditioning and conventional high-dose conditioning for allogeneic hematopoietic stem cell transplantation using HLA-identical sibling donors in myelodysplastic syndromes, Blood, 108:836-846 (2006).

Medyouf, H. et al., Myelodysplastic cells in patients reprogram mesenchymal stromal cells to establish a transplantable stem cell niche disease unit, Cell Stem Cell, 14:824-837 (2014).

Mossner, M. et al., Mutational hierarchies in myelodysplastic syndromes dynamically adapt and evolve upon therapy response and failure, Blood, 128:1246-1259 (2016).

Rissin, D. et al., Single-molecule enzyme-linked immunosorbent assay detects serum proteins at subfemtomolar concentrations, Nat. Biotechnol., 28:595-599 (2010).

Schilter, H. et al., The lysyl oxidase like 2/3 enzymatic inhibitor, PXS-5153A, reduces crosslinks and ameliorates fibrosis, J. Cell Mol. Med., 23:1759-1770 (2018).

Sierra, J. et al., Bone marrow transplantation from HLA-identical siblings as treatment for myelodysplasia, Blood, 100:1997-2004 (2002).

Sloand, E. M. et al., Factors affecting response and survival in patients with myelodysplasia treated with immunosuppressive therapy, J. Clin. Oncol., 26:2505-2511 (2008).

Spivak, J.L., Myeloproliferative Neoplasms, N Engl J Med, 376:2168-2181 (2017).

Tanaka, T. et al., MDS overlap disorders and diagnostic boundaries, Blood, 133:1086-1095 (2019).

Witte, T. et al., Intensive chemotherapy followed by allogeneic or autologous stem cell transplantation for patients with myelodysplastic syndromes (MDSs) and acute myeloid leukemia following MDS, Blood, 98:2326-2331 (2001).

* cited by examiner

LYSYL OXIDASE INHIBITORS FOR TREATING MYELOID MALIGNANCIES

CROSS-REFERENCE TO RELATED APPLICATION

This application is a United States Nonprovisional Application filed on Apr. 5, 2023, which application claims the benefit of priority from Australian Provisional Application No. 2022900904, filed on Apr. 6, 2022. The contents and disclosure of the foregoing application are incorporated by reference herein in their entireties.

TECHNICAL FIELD

The present invention relates to methods for the treatment of myeloid malignancies, such as myelodysplastic syndromes (MDS), by administration of a lysyl oxidase inhibitor. The lysyl oxidase inhibitor can be administered alone or in combination with a second therapeutic agent.

BACKGROUND

Myeloid Malignancies

Myeloid malignancies (or neoplasms) encompass a diverse and heterogeneous group of clonal diseases that emerge in hematopoietic stem cells (HSC) and interfere with normal myeloid cell production and differentiation.

Myeloid neoplasia is divided into four major categories based on a combination of clinical presentation and cytogenetic abnormalities:
  Myelodysplastic syndromes (MDS)
  Acute myeloid leukemia (AML), including acute promyelocytic leukemia (APL; a distinct subset of AML)
  Myeloproliferative neoplasms (MPN)
  MDS/MPN overlap syndromes Symptoms in these conditions generally arise as a result of cytopenias, extramedullary hematopoiesis causing splenomegaly, vascular and/or venous thrombohemorrhagic complications, or constitutional symptoms. The genetic abnormalities that underlie myeloid neoplasia are diverse. However, the affected cells of individual patients typically show only a few discrete, recurrent mutations. These mutations arise in genes whose function can be organized into eight categories, including [1]:
  Transcription factors
  Signal transduction kinases and phosphatases
  Genes controlling DNA methylation
  Post-translational chromatin modifiers
  RNA splicing machinery
  The cohesion complex
  Tumor suppressors
  Gene encoding nucleophosmin-1

Myelodysplastic Syndromes

Myelodysplastic syndromes encompass a collection of hematological neoplasms characterized by varying degrees of cytopenias, morphological and functional abnormalities of hematopoietic cells ultimately resulting in ineffective hematopoiesis. MDS further confers a predisposition to acute myeloid leukemia (AML). Traditionally, studies have focused on hematopoietic cells in an effort to understand hematologic disease development with the ultimate goal of implementing therapeutic solutions. The hematopoietic cells in MDS have been shown to contain numerous genetic and epigenetic abnormalities and these studies have helped elucidate the pathophysiology of MDS [2].

The first International Prognostic Scoring System (IPSS) was derived from a study published in 1997 and classifies MDS patients into four categories: low risk, intermediate-1 risk, intermediate-2 risk, and high risk. This was subsequently revised in 2012 (IPSS-R) and separates patients into five categories: very low risk, low risk, intermediate risk, high risk, and very high risk. The World Health Organisation (WHO) classifies MDS into several sub-types based on morphologic and cytogenetic information:
  Refractory cytopenia with unilineage dysplasia (includes refractory anaemia (RA), refractory neutropenia (RN) and refractory thrombocytopenia (RT))
  Refractory anemia with ringed sideroblasts (RARS)
  Refractory cytopenia with multilineage dysplasia (RCMD)
  Refractory cytopenia with multilineage dysplasia and ringed sideroblasts (RCMD-RS)
  Refractory anemia with excess blasts type 1 (RAEB-1), and type 2 (RAEB-2)
  Myelodysplastic syndrome, unclassified (MDS-U)
  MDS associated with isolated del (5q).

Myelodysplastic syndromes are further classified as primary (or de novo) MDS which originate spontaneously (usually from somatic or acquired gene mutation) without a history of therapy (cytotoxic or radiotherapy), or secondary MDS which results from a complication of therapy. These classification systems are used in an integrated manner to direct clinical decision-making, risk stratification and determine appropriate patient treatment [2].

Studies have demonstrated a clear correlation between prevalence of MDS and age, and provide a biological rationale for why MDS often presents in the seventh and eight decades of life. The incidence of MDS has escalated in recent years due to longer life expectancy and an increasing elderly population. It is conservatively estimated that >10,000 new cases are presented in the United States annually, with >60,000 individuals with MDS currently residing in the country [3]. A large majority of MDS cases have no obvious risk factor. Familial MDS presenting in childhood occurs rarely and usually arises from inherited mutations in DNA repair enzymes or telomere maintenance [4], [5]. Chronic exposure to certain chemical agents (e.g., benzene and certain pesticides), smoking, as well as previous chemotherapy/radiotherapy are the biggest risk factors for sporadic MDS [2].

The most common cause of death in patients with MDS is bone marrow failure, immune dysfunction and/or transformation to AML. Current treatment options for MDS are limited. They include allogeneic hematopoietic stem cell (HSC) transplantation [6], [7], [8], [9], [10], [11], erythropoiesis-stimulating agents, intensive chemotherapy [12], epigenetic modifying drugs, hypomethylating agents [13] or other novel targeted therapies [14]. While HSC transplantation can be used as a curative treatment for MDS, this option is unavailable to many older patients, who instead receive supportive care and transfusions to ameliorate anaemia and other disease complications. Even after HSC transplantation, MDS clones can persist in the marrow, and the disease invariably progresses. Despite recent progress, most MDS patients exhibit treatment-related toxicities or relapse. Overall, the efficacy of these treatments is variable, and generally life expectancies are only slightly improved as compared to supportive care [2].

Acute Myeloid Leukemia

Acute myeloid leukemia (AML) is a heterogeneous collection of leukemias that arise in precursors of myeloid cell lineages. They are characterised by rapid clonal expansion of the myeloid cells whose maturation is arrested at the myoblast stage, ultimately leading to ineffective hematopoiesis. These leukemias result from a number of genetic events including chromosomal rearrangement and amplification, translocations and deletions, as well as point mutations, insertions and tandem duplications. As with all other myeloid disease subtypes, an understanding of the genetic complement of AML is key for accurate diagnosis, prognostics and therapeutics. In the US 4.1/100,000 persons/year present with AML and this rate increases with age. There are approximately 21,000 new cases of AML in the US each year with approximately 10,500 deaths. AML can be preceded by either MDS or MPN. However, in most cases, AML arises de novo. Risk factors include exposure to cytotoxic chemotherapy, ionizing radiation, tobacco smoke and benzene. Childhood-onset AML (familial AML) is rare and result from inherited defective DNA repair enzymes. Despite substantial evidence for environmental carcinogens and/or impaired host response to DNA damage as causative factors, >95% of AML patients have no identifiable risk factor.

Myeloproliferative Neoplasms

Myeloproliferative neoplasms (MPN) are characterized by clonal proliferation of some or all myeloid lineages (depending on the sub-type) leading to a corresponding elevation of peripheral blood counts [15]. MPNs arise as a result of acquisition of somatic mutations in a single HSC that confers a selective advantage over normal HSC and promote myeloid differentiation to beget a myeloproliferative phenotype. According to the WHO classification system (2017 revision), MPNs broadly encompass seven sub-categories of diseases:

Chronic myeloid leukemia (CML)
Chronic neutrophilic leukemia (CNL)
Chronic eosinophilic leukemia (CEL)
Polycythemia vera (PV)
Essential thrombocythemia (ET)
Primary myelofibrosis (PMF)
MPN unclassifiable (MPN-U)

The most prevalent disease-initiating driver mutation occurs in the janus kinase 2 (JAK2) gene, JAK2 V617F. This results in constitutive JAK-signal transducer and activator of transcription (JAK-STAT) signalling and ultimately interference in gene transcription. Dysregulation of this signalling pathway has been identified in all MPNs. Other significant driver mutations that contribute to the phenotypic heterogeneity of MPNs include the gene encoding calreticulin (CALR), and the thrombopoietin receptor gene, MPL. Clinical manifestations common to all subtypes of MPNs are increased risk of vascular complications including arterial/venous thrombosis, significant constitutional burden (e.g., night sweat, anorexia and weight loss). These are in turn related to the systemic inflammatory state caused by proinflammatory cytokines released. Furthermore, there is an increased risk of progression to AML. Aside from driver mutations, patient characteristics including gender, age, comorbidities and environmental exposure are known factors that contribute to disease phenotype. The incidence of MPN increases with age and, in fact, age is also the most significant determinant of MPN disease heterogeneity in terms of thrombosis risk, disease progression and long-term survival [15].

Despite common biological features, MPNs display diverse disease phenotypes—the spectrum of clinical phenotypes can range from completely asymptomatic patients to those with debilitating disease. This results from both constitutional and acquired factors that influence MPN stem cells, and likely also stems from heterogeneity in the HSC in which MPN-initiating mutations arise. As the MPN clone expands, it exerts cell-extrinsic effects on components of the bone marrow niche that can favour the survival and expansion of MPN stem cells over normal HSC, further sustaining and fostering malignant hematopoiesis. There is also considerable overlap in clinical features between MPN subtypes. This can make diagnosis challenging and limit the ability to provide accurate diagnosis. Although developed as targeted therapies for MPNs, current JAK2 inhibitors do not preferentially target MPN stem cells, and as a result, rarely induce molecular remissions in MPN patients [15].

Overlap MDS/MPN Neoplasms

By definition, overlap MDS/MPN has features characteristic of both MDS and MPN; complicating assignment to any one category. The World Health Organization classification coined this designation in 2008 to include:

Chronic myelomonocytic leukemia (CMML)
Juvenile myelomonocytic leukemia (JMML)
Atypical chronic myeloid leukemia (aCML)
Refractory anaemia with ring sideroblasts and thrombocytosis (RARS-T; provisional entry)
MDS/MPN unclassified (MDS/MPN-U)

Cytogenetic abnormalities are identified in almost 70% of patients with MDS/MPN. Somatic mutations observed fall into 4 major categories: signalling, splicing, epigenetic, and transcription gene mutations [16].

A critical step in the management of MDS/MPN is establishing accurate diagnosis, with treatment strategies largely adapted from available therapies for MDS and MPN.

Lysyl Oxidase Family of Enzymes

The lysyl oxidase (LOX) family of enzymes consists of five members: lysyl oxidase (LOX), lysyl oxidase-like 1 (LOXL1), lysyl oxidase-like 2 (LOXL2), lysyl oxidase-like 3 (LOXL3) and lysyl oxidase-like 4 (LOXL4), which are copper and lysine tyrosyl-quinone (LTQ)-dependent amine oxidases. The canonical function of LOX enzymes is to catalyze the crosslinking of collagen and elastin. In this way, they are involved in one of the final post-translational modifications of collagen, where collagen fibrils, comprised of mature tropocollagen molecules bundled in parallel, are stabilized by the formation of covalent cross-links between adjacent fibrils. Similarly, the LOX family members also catalyze the oxidation of lysines in tropoelastin, resulting in stabilized cross-links between them to form strong, durable and flexible elastin microfibrils. Effectively, these cross-links provide structural integrity to mature collagen and elastin sheets formed within the extracellular matrix (ECM), and may additionally protect these matrix molecules against proteolytic degradation. Lysyl oxidase isoenzymes belong to a larger group of copper-dependent, amine oxidases which include flavin-dependent and copper-dependent oxidases which are described by the nature of the catalytic co-factor. Flavin-dependent enzymes include monoamine oxidase-A (MAO-A), monoamine oxidase-B (MAO-B), polyamine oxidase and lysine demethylase (LSD1), and the copper-dependent enzymes including semicarbazide sensitive amine oxidase (vascular adhesion protein-1, SSAO/VAP-1), retinal amine oxidase and diamine oxidase. Human LOX and LOXL1-4 proteins are expressed in several different tissues and organs [17].

Lysyl oxidase isoenzymes exhibit different in vivo expression patterns, which suggests that specific isoenzymes will have specific biological roles. Catalytically active lysyl oxidases have been identified in the cytosolic and nuclear compartments and evidence is growing to support a role for LOX in other critical biological functions, including gene expression regulation, cell growth, adhesion and migration. Accordingly, recent studies support a pivotal role of LOX in cancer progression and metastasis [17].

New molecular technologies, and genomics continue to play an important role in the corridor to a better understanding of the myriad of molecular events that underlie myeloid diseases. They guide and improve classification of the multiple subtypes according to risk and provide invaluable insight that enables the development of targeted therapies. On a patient level, the improved understanding of the complex biology behind myeloid diseases translates to better diagnosis, prognosis, and treatment options beyond supportive care. Despite this advancement in understanding, there remains a clear need for the development of better, more specific, molecularly targeted therapies.

The inventors have found that LOX and LOXL inhibitors, alone or in combination with a second therapeutic agent, are effective in the treatment of myeloid malignancies, including MDS.

SUMMARY

Patients afflicted with myeloid malignancies have limited treatment options that can offer a meaningful long-term response. Therefore, there remains an unmet need for new treatments for myeloid malignancies. Disclosed herein is a method for treating myeloid malignancies in a subject that involves administering a therapeutically effective amount of a lysyl oxidase inhibitor. In one embodiment the myeloid malignancy is myelodysplastic syndrome (MDS).

A first aspect of the invention provides for a method for the treatment of a myeloid malignancy in a subject, the method comprising administering to the subject a therapeutically effective amount of a lysyl oxidase (LOX) inhibitor, a lysyl oxidase-like (LOXL) inhibitor, or a pharmaceutically acceptable salt thereof.

A second aspect of the invention provides for a method for the treatment of a myeloid malignancy in a subject, the method comprising administering to the subject a first composition comprising a therapeutically effective amount of a lysyl oxidase (LOX) inhibitor, a lysyl oxidase-like (LOXL) inhibitor, or a pharmaceutically acceptable salt thereof; and a second composition comprising one or more additional therapeutic agents.

In one embodiment the myeloid malignancy is selected from the group consisting of myelodysplastic syndromes (MDS), myeloproliferative neoplasms (MPN), MDS/MPS overlap syndromes, especially CMML and acute myeloid leukemia (AML), including acute promyelocytic leukemia (APL). In another embodiment the myeloid malignancy is myelodysplastic syndrome (MDS).

In one embodiment the LOX or LOXL inhibitor is

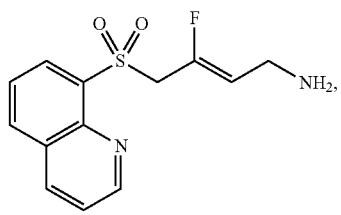 [SMILES: NC/C=C(\F)CS(=O)(=O)c1cccc2cccnc12]

or a pharmaceutically acceptable salt thereof.

A third aspect of the invention provides for a method for the treatment of myelodysplastic syndrome (MDS) in a subject, the method comprising administering to the subject a first composition comprising a therapeutically effective amount of a lysyl oxidase (LOX) inhibitor, a lysyl oxidase-like (LOXL) inhibitor, or a pharmaceutically acceptable salt thereof; and a second composition comprising one or more additional therapeutic agents, wherein the LOX or LOXL inhibitor is

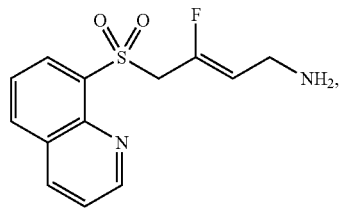 [SMILES: NC/C=C(\F)CS(=O)(=O)c1cccc2cccnc12]

or a pharmaceutically acceptable salt thereof and the additional therapeutic agent is 5-azacytidine or a pharmaceutically acceptable salt thereof.

A fourth aspect of the invention provides for a method for the treatment of myelodysplastic syndrome (MDS) in a subject, the method comprising administering to the subject a first composition comprising a therapeutically effective amount of a lysyl oxidase (LOX) inhibitor, a lysyl oxidase-like (LOXL) inhibitor, or a pharmaceutically acceptable salt thereof; and a second composition comprising one or more additional therapeutic agents, wherein the LOX or LOXL inhibitor is

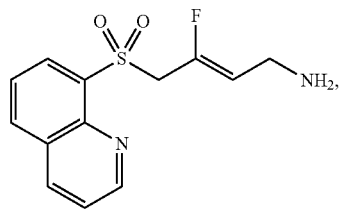 [SMILES: NC/C=C(\F)CS(=O)(=O)c1cccc2cccnc12]

or a pharmaceutically acceptable salt thereof and the additional therapeutic agent is decitabine or a pharmaceutically acceptable salt or orally bioavailable cedazuridine combination product thereof.

A further aspect of the invention provides for use of a lysyl oxidase (LOX) inhibitor, a lysyl oxidase-like (LOXL) inhibitor, or a pharmaceutically acceptable salt thereof for the manufacture of a medicament for the treatment of myeloid malignancy, such as myelodysplastic syndrome (MDS).

Another aspect of the invention provides for a lysyl oxidase (LOX) inhibitor, a lysyl oxidase-like (LOXL) inhibitor, or a pharmaceutically acceptable salt thereof for use in the treatment of a myeloid malignancy, such as myelodysplastic syndrome (MDS).

The lysyl oxidase inhibitor can be administered alone or in combination with other therapies useful for the treatment of a myeloid malignancy, such as myelodysplastic syndrome (MDS).

In one embodiment the LOX or LOXL inhibitor and the one or more additional therapeutic agents act synergistically in the treatment of the myeloid malignancy, such as myelodysplastic syndrome (MDS).

Definitions

The following are some definitions that may be helpful in understanding the description of the present invention.

These are intended as general definitions and should in no way limit the scope of the present invention to those terms alone, but are put forth for a better understanding of the following description.

Unless the context requires otherwise or specifically states to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein, the term "alkyl" includes within its meaning monovalent ("alkyl") and divalent ("alkylene") straight chain or branched chain saturated hydrocarbon radicals having from 1 to 6 carbon atoms, e.g., 1, 2, 3, 4, 5 or 6 carbon atoms. The straight chain or branched alkyl group is attached at any available point to produce a stable compound. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

The term "alkoxy" or "alkyloxy" as used herein refers to straight chain or branched alkyloxy (i.e, O-alkyl) groups, wherein alkyl is as defined above. Examples of alkoxy groups include methoxy, ethoxy, n-propoxy, and isopropoxy.

The term "cycloalkyl" as used herein includes within its meaning monovalent ("cycloalkyl") and divalent ("cycloalkylene") saturated, monocyclic, bicyclic, polycyclic or fused analogs. In the context of the present disclosure the cycloalkyl group may have from 3 to 10 carbon atoms. A fused analog of a cycloalkyl means a monocyclic ring fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, adamantyl and the like.

The term "aryl" or variants such as "arylene" as used herein refers to monovalent ("aryl") and divalent ("arylene") single, polynuclear, conjugated and fused analogs of aromatic hydrocarbons having from 6 to 10 carbon atoms. A fused analog of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, tetrahydrobenzopyranyl, 1,4-benzodioxanyl, and the like. A "substituted aryl" is an aryl that is independently substituted, with one or more, preferably 1, 2 or 3 substituents, attached at any available atom to produce a stable compound.

The term "alkylaryl" as used herein, includes within its meaning monovalent ("aryl") and divalent ("arylene"), single, polynuclear, conjugated and fused aromatic hydrocarbon radicals attached to divalent, saturated, straight or branched chain alkylene radicals. Examples of alkylaryl groups include benzyl.

The term "heteroaryl" and variants such as "heteroaromatic group" or "heteroarylene" as used herein, includes within its meaning monovalent ("heteroaryl") and divalent ("heteroarylene"), single, polynuclear, conjugated and fused heteroaromatic radicals having from 5 to 10 atoms, wherein 1 to 4 ring atoms, or 1 to 2 ring atoms are heteroatoms independently selected from O, N, NH and S. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. The heteroaromatic group may be $C_{1-9}$heteroaromatic. A fused analog of heteroaryl means a heteroaryl group fused to a monocyclic cycloalkyl or monocyclic heterocyclyl group in which the point of attachment is on the aromatic portion. Examples of heteroaryl groups and fused analogs thereof include pyrazolyl, pyridyl, oxazolyl, oxadiazolyl, thiadiazolyl, tetrazolyl, triazinyl, thienyl, benzoxazolyl, benzothiazolyl, benzimidazolyl, benzofuranyl, benzothiophenyl, furo(2,3-b)pyridyl, indolyl, isoquinolyl, imidazopyridyl, pyrimidinyl, pyridazinyl, pyrazinyl, pyridonyl, phenanthrolinyl, quinolyl, isoquinolinyl, imidazolinyl, thiazolinyl, pyrrolyl, furanyl, thiophenyl, oxazolyl, isoxazolyl, isothiazolyl, triazolyl, and the like. "Nitrogen containing heteroaryl" refers to heteroaryl wherein any heteroatoms are N. A "substituted heteroaryl" is a heteroaryl that is independently substituted, with one or more, preferably 1, 2 or 3 substituents, attached at any available atom to produce a stable compound.

The term "heterocyclyl" and variants such as "heterocycloalkyl" as used herein, includes within its meaning monovalent ("heterocyclyl") and divalent ("heterocyclylene"), saturated or partially saturated (non-aromatic), monocyclic, bicyclic, polycyclic or fused hydrocarbon radicals having from 3 to 10 ring atoms, wherein from 1 to 4, or from 1 to 2, ring atoms are heteroatoms independently selected from O, N, NH, or S, SO or $SO_2$, in which the point of attachment may be carbon or nitrogen. A fused analog of heterocyclyl means a monocyclic heterocycle fused to an aryl or heteroaryl group in which the point of attachment is on the non-aromatic portion. The heterocyclyl group may be $C_{3-5}$ heterocyclyl. The heterocycloalkyl group may be $C_{3-6}$ heterocyclyl. The heterocyclyl group may be $C_{3-5}$ heterocyclyl. Examples of heterocyclyl groups and fused analogs thereof include pyrrolidinyl, thiazolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, quinuclidinyl, azetidinyl, morpholinyl, tetrahydrothiophenyl, tetrahydrofuranyl, tetrahydropyranyl, and the like. The term also includes partially unsaturated monocyclic rings that are not aromatic, such as 2- or 4-pyridones attached through the nitrogen or N-substituted uracils.

The term "halogen" or variants such as "halide" or "halo" as used herein refers to fluorine, chlorine, bromine and iodine.

The term "heteroatom" or variants such as "hetero-" or "heterogroup" as used herein refers to O, N, NH and S.

In general, "substituted" refers to an organic group as defined herein (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, hydroxyl, hydroxyalkyl, alkoxy, thioalkoxy, alkenyloxy, haloalkoxy, $NO_2$, NH(alkyl), N(alkyl)$_2$, alkylamino, dialkylamino, acyl, alkenoyl, alkynoyl, acylamino, diacylamino, acyloxy, alkylsulfonyl, alkylsulfonyloxy, sulfonamido, heterocycloxy, heterocycloamino, haloheterocycloalkyl, alkylsulfenyl, alkylcarbonyloxy, phosphorus-containing groups such as phosphono and phosphinyl, aryl, heteroaryl, alkylaryl, aralkyl, alkylheteroaryl, cyano, $CO_2H$, $CO_2$alkyl, $C(O)NH_2$, —C(O)NH(alkyl), and —C(O)N(alkyl)$_2$. Preferred substituents include halogen, $C_1$-$C_6$alkyl, $C_1$-$C_6$haloalkyl, $C_1$-$C_6$alkoxy, hydroxy($C_{1-6}$)alkyl, $C_3$-$C_6$cycloalkyl, C(O)OH, NHC(O)$C_1$-$C_4$alkyl, $C(O)C_1$-$C_4$alkyl, $NH_2$, $NHC_1$-$C_4$alkyl, $N(C_1$-$C_4$alkyl)$_2$, $SO_2(C_1$-$C_4$alkyl), OH and CN. Particularly preferred substituents include $C_{1-4}$alkyl, $C_{1-4}$alkoxy, $SO_2(C_1$-$C_4$alkyl), halogen, OH, hydroxy($C_{1-3}$)alkyl (e.g. $C(CH_3)_2OH$), and $C_{1-3}$haloalkyl (e.g. $CF_3$, $CH_2CF_3$).

In the context of this specification the term "administering" and variations of that term including "administer" and "administration", includes contacting, applying, delivering or providing a compound or composition of the invention to an organism, or a surface by any appropriate means. In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

In the context of this specification the term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

In the context of this specification, the term "synergistic effect" refers to a phenomenon whereby two chemical agents interact or cooperate to give rise to a result that is greater than the sum of the contribution of the two chemical agents alone.

All references cited in this application are specifically incorporated by cross-reference in their entirety. Reference to any such documents should not be construed as an admission that the document forms part of the common general knowledge or is prior art.

BRIEF DESCRIPTION OF THE FIGURES AND TABLE

Figure 3:
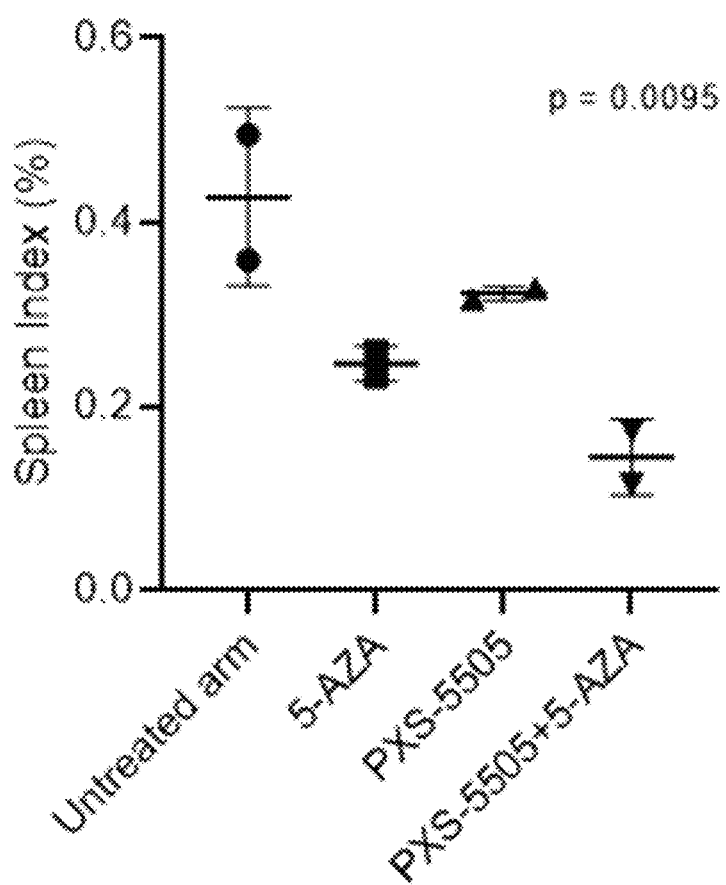

FIG. 3 depicts data from a xenotransplantation model. The spleen index is reduced after combination treatment with 5-AZA and PXS-5505. The single treatments of 5-AZA and PXS-5505 show a similar trend of reducing the spleen index.

Figure 4:
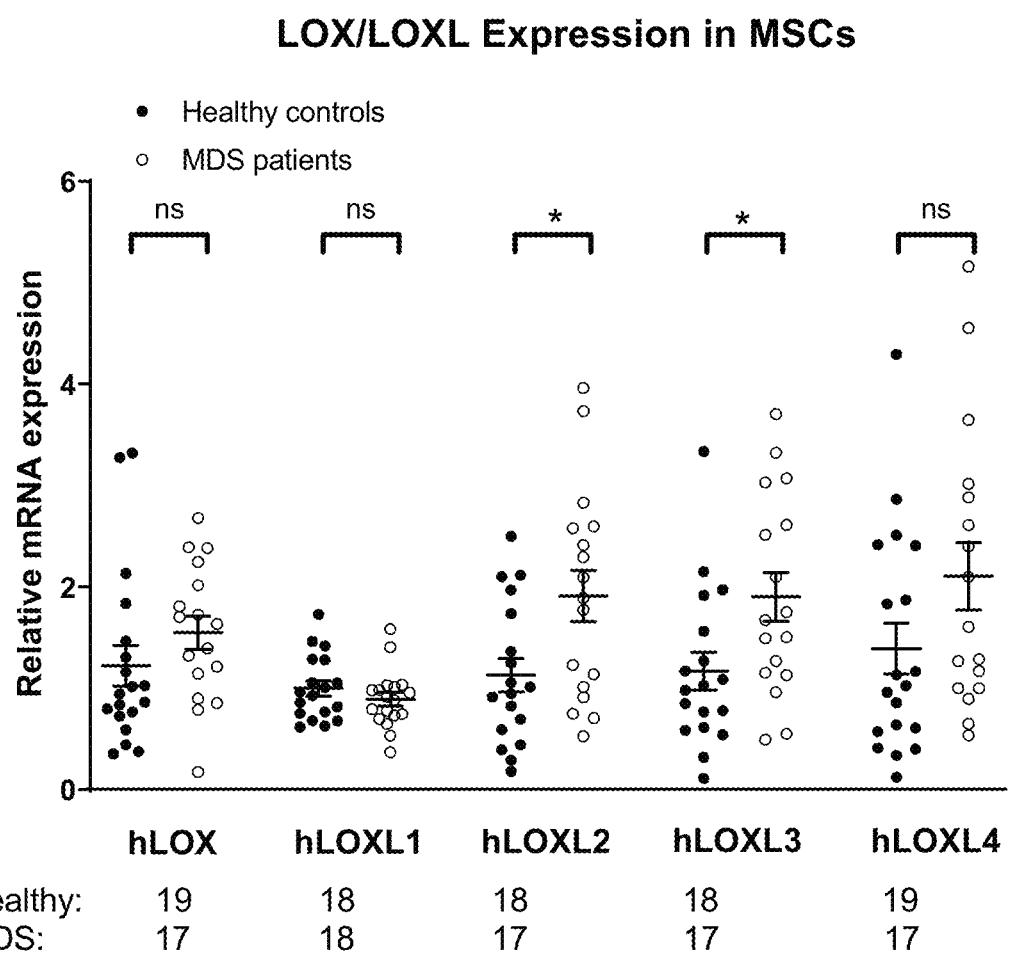

FIG. 4 shows an increase in expression of several of the lysyl oxidases (LOX, LOXL1, LOXL2, LOXL3 and LOXL4) in bone marrow aspirates of MDS patients compared to healthy controls.

Figure 5:
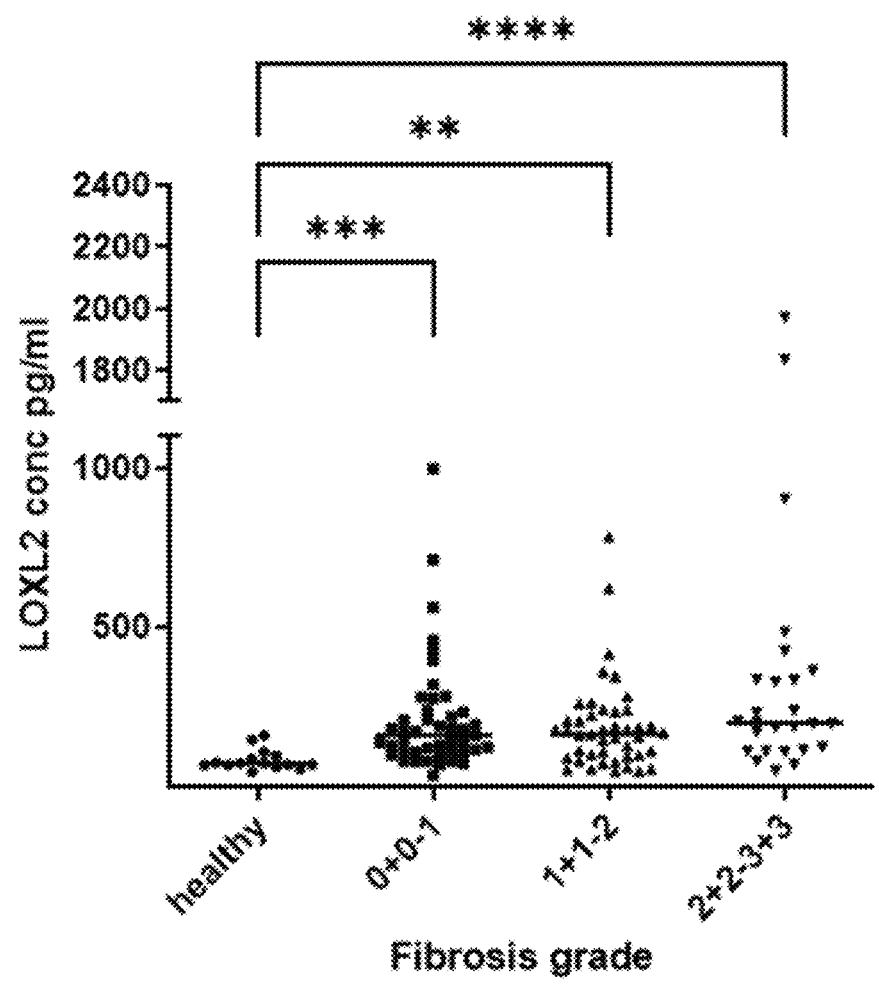

FIG. 5 shows that LOXL2 protein concentration in patient bone marrow aspirates, as measured by the Simoa™ assay, increases with increasing fibrosis score in MDS patients.

Figure 6:
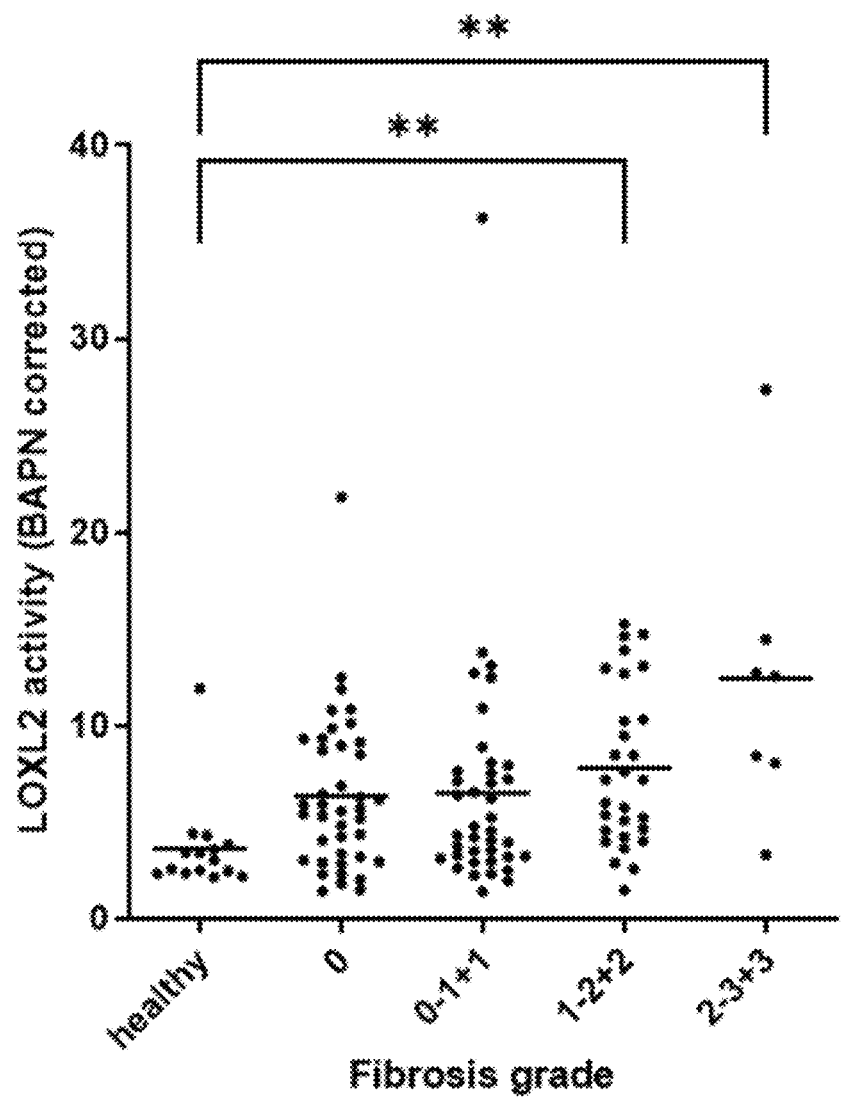

FIG. 6 shows that MDS patients bone marrow aspirates display an increase in LOXL2 activity, that is associated with increased fibrosis score.

DETAILED DESCRIPTION

Treatment of Myeloid Malignancies

The present invention provides for methods of treating myeloid malignancies. A first aspect of the invention provides for a method for the treatment of a myeloid malignancy in a subject, the method comprising administering to the subject a therapeutically effective amount of a lysyl oxidase (LOX) inhibitor, a lysyl oxidase-like (LOXL) inhibitor, or a pharmaceutically acceptable salt thereof.

In one embodiment the myeloid malignancy is selected from the group consisting of myelodysplastic syndromes (MDS), myeloproliferative neoplasms (MPN), MDS/MPS overlap syndromes and acute myeloid leukemia (AML), including acute promyelocytic leukemia (APL).

In one embodiment the myeloid malignancy is myelodysplastic syndrome (MDS).

In some embodiments of the methods of the present invention the MDS is characterized by refractory anemia (RA), refractory neutropenia (RN), and/or refractory thrombocytopenia (RT). In some embodiments, the MD S is characterized by refractory anemia (RA) with ringed sideroblasts (RARS). In some embodiments, the MD S is characterized by refractory cytopenia with multilineage dysplasia (RCMD). In some embodiments, the MDS is characterized by refractory cytopenia with multilineage dysplasia and ringed sideroblasts (RCMD-RS). In some embodiments, MDS is characterized by refractory anemia (RA) with excess blasts-1 (RAEB-1). In some embodiments, the MDS is characterized by refractory anemia (RA) with excess blasts-2 (RAEB-2). In some embodiments, the MDS is characterized by refractory anemia (RA) with excess blasts in transformation (RAEB-t). In some embodiments, the MDS is unclassified myelodysplastic syndrome (MDS-U). In some embodiments the MDS is associated with isolated del (5q).

In some embodiments of the methods of the present invention the MDS is primary MDS which originate spontaneously without a history of therapy or secondary MDS where the MDS result from a complication of therapy. In one embodiment of the methods of the present invention the MDS is primary MDS. In another embodiment of the methods of the present invention the MDS is secondary MDS.

In some embodiments of the methods of the present invention, the MDS in the subject is low risk MDS based on the IPSS system. In some embodiments, the MDS in the subject is intermediate-1 risk MDS based on the IPSS system. In some embodiments, the MDS in the subject is intermediate-2 risk MDS based on the IPSS system. In some embodiments, the MDS in the subject is high risk MDS based on the IPSS system.

The present invention relates to use of compounds in the treatment of myeloid malignancies, such as MDS, in particular to inhibit members of the lysyl oxidase family members, LOX, LOXL1, LOXL2, LOXL3 and LOXL4. In one embodiment, the invention provides for the inhibition of specific lysyl oxidase isoenzymes. In another embodiment, the invention provides for the simultaneous inhibition of 2, 3, 4 or 5 lysyl oxidase isoenzymes.

In one embodiment the invention provides for the treatment of MDS by inhibition of LOX. In another embodiment the invention provides for the treatment of MDS by inhibition of LOXL1. In a further embodiment the invention provides for the treatment of MDS by inhibition of LOXL2. In another embodiment the invention provides for the treatment of MDS by inhibition of LOXL3. In a further embodiment the invention provides for the treatment of MDS by inhibition of LOXL4. In a further embodiment the invention provides for the treatment of MDS by inhibition of LOX and LOXL1 and LOXL2 and LOXL3 and LOXL4.

The present invention further provides for use of a lysyl oxidase (LOX) inhibitor, a lysyl oxidase-like (LOXL) inhibitor, or a pharmaceutically acceptable salt thereof for the manufacture of a medicament for the treatment of myeloid malignancies, including myelodysplastic syndrome (MDS).

Also disclosed is a lysyl oxidase (LOX) inhibitor, a lysyl oxidase-like (LOXL) inhibitor, or a pharmaceutically acceptable salt thereof, for use in the treatment of myeloid malignancies, including myelodysplastic syndrome (MDS).

Combination Therapy

In accordance with another aspect of the present invention, it is contemplated that the LOX or LOXL inhibitor as described herein may be administered to a subject in need thereof in combination with medication considered by those of skill in the art to be current standard of care for the treatment of myeloid malignancies, including myelodysplastic syndrome (MDS). Such combinations provide one or more advantages to the subject, e.g., requiring reduced dosages to achieve similar benefit, obtaining the desired therapeutic effect in less time, and the like.

LOX or LOXL inhibitors may be administered as part of a therapeutic regimen with other drugs. It may be desirable to administer a combination of active compounds, for example, for the purpose of treating myeloid malignancies, including myelodysplastic syndrome (MDS). Accordingly, it is within the scope of the present invention that two or more pharmaceutical compositions, at least one of which contains a LOX or LOXL inhibitor, may be combined in the form of a kit suitable for co-administration of the compositions.

A second aspect of the invention provides for a method for the treatment of a myeloid malignancy in a subject, the method comprising administering to the subject a first composition comprising a therapeutically effective amount of a lysyl oxidase (LOX) inhibitor, a lysyl oxidase-like (LOXL) inhibitor, or a pharmaceutically acceptable salt thereof; and a second composition comprising one or more additional therapeutic agents.

In one embodiment of the methods of the present inventions the LOX or LOXL inhibitor may be administered with one or more additional therapeutic agents.

In some embodiments the lysyl oxidase inhibitor may be administered in combination with, or in conjunction with an additional therapeutic agent potentially useful in the treatment of myeloid disease, such as a hypomethylating agent, for example: 5-azacytidine, decitabine or guadecitabine. In one embodiment the additional therapeutic agent is 5-azacytidine. In one embodiment 5-azacytidine is administered in combination with a further additional therapeutic agent. In one embodiment the additional therapeutic agent is decitabine. In one embodiment decitabine is administered in combination with a further additional therapeutic agent. In one embodiment decitabine is administered orally in a further additional combination with cedazuridine, In some embodiments the lysyl oxidase inhibitor may be administered in combination with, or in conjunction with an additional therapeutic agent potentially useful in the treatment of myeloid disease, such as a protein translation inhibitor, for example omacetaxine, In some embodiments the lysyl oxidase inhibitor may be administered in combination with, or in conjunction with an additional therapeutic agent potentially useful in the treatment of myeloid disease, such as a ribonucleotide reductase inhibitor, for example hydroxyurea.

In some embodiments the lysyl oxidase inhibitor may be administered in combination with, or in conjunction with an additional therapeutic agent potentially useful in the treatment of myeloid disease, such as an inhibitor of platelet maturation, for example anagrelide.

In some embodiments the lysyl oxidase inhibitor may be administered in combination with, or in conjunction with an additional therapeutic agent potentially useful in the treatment of myeloid disease, such as a stimulator of telomerase activity, for example danazol.

In some embodiments the lysyl oxidase inhibitor may be administered in combination with, or in conjunction with an additional therapeutic agent potentially useful in the treatment of myeloid disease, such as, but not limited to, a red blood cell growth factor, a white blood cell growth factor, a platelet growth factor, granulocyte macrophage-colony stimulating factor, erythropoietin, pegfilgrastim, darbepoetin alfa, oprelvekin, arsenic trioxide, luspatercept, erythropoiesis stimulating agents, iron chelating therapeutics, androgen therapeutics.

In some embodiments the lysyl oxidase inhibitor may be administered in combination with, or in conjunction with an additional therapeutic agent potentially useful in the treatment of myeloid disease, such as, but not limited to an S100A8/S100A9 inhibitor such as tasquinimod, paquinimod and laquinimod.

In some embodiments the lysyl oxidase inhibitor may be administered in combination with, or in conjunction with an additional therapeutic agent potentially useful in the treatment of myeloid disease, such as, but not limited to a hedgehog inhibitor.

In some embodiments the lysyl oxidase inhibitor may be administered in combination with, or in conjunction with an additional therapeutic agent potentially useful in the treatment of myeloid disease, such as, but not limited to an IDH1/IDH2 inhibitor such as enasidenib or ivosidenib.

In some embodiments the lysyl oxidase inhibitor may be administered in combination with, or in conjunction with an additional therapeutic agent potentially useful in the treatment of myeloid disease, such as, but not limited to a GANT61 inhibitor.

In some embodiments the lysyl oxidase inhibitor may be administered in combination with, or in conjunction with an additional therapeutic agent potentially useful in the treatment of myeloid disease, such as, but not limited to canakinumab, bortezomib, CC-486, epacadostat, infliximab, mycophenolate (plus prednisone), siltuximab, tomaralimab, ezatiostat, BI 836858, tipifarnib, ASTX727, pexmetinib, AZD6738, rigosertib and alvocidib.

In some embodiments the lysyl oxidase inhibitor may be administered in combination with, or in conjunction with an additional therapeutic agent potentially useful in the treatment of myeloid disease, such as an inducer of HSC mobilization, for example granulocyte colony stimulating factor In some embodiments the lysyl oxidase inhibitor may be administered in combination with, or in conjunction with an additional therapeutic agent potentially useful in the treatment of myeloid disease, such as an immunomosuppressant, for example cyclosporine, prednisone or methotrexate In some embodiments the lysyl oxidase inhibitor may be administered in combination with, or in conjunction with an additional therapeutic agent potentially useful in the treatment of myeloid disease, such as an agent that reduces Smad2/3 signalling, for example laspatercept, In some embodiments the lysyl oxidase inhibitor may be administered in combination with, or in conjunction with an additional therapeutic agent potentially useful in the treatment of myeloid disease, such as an immunomodulatory agent, for example thalidomide, pomalidomide, anti-thymocyte globulin or interferon-α

In some embodiments the lysyl oxidase inhibitor may be administered in combination with, or in conjunction with an additional therapeutic agent potentially useful in the treatment of myeloid disease, such as an activator of apoptosis, for example lenalidomide In some embodiments the lysyl oxidase inhibitor may be administered in combination with, or in conjunction with an additional therapeutic agent potentially useful in the treatment of myeloid disease, such as an antimetabolite antineoplastic agent, for example: cytarabine, clofarabine, cedazuridine or 6-mercaptopurine In some embodiments the lysyl oxidase inhibitor may be administered in combination with, or in conjunction with an additional therapeutic agent potentially useful in the treatment of myeloid disease, such as an antitumour antibiotic, for example: idarubicin, daunorubicin or doxorubicin In some embodiments the lysyl oxidase inhibitor may be administered in combination with, or in conjunction with an additional therapeutic agent potentially useful in the treatment of myeloid disease, such as a topoisomerase inhibitor, for example: topotecan or anthracycline.

In some embodiments the lysyl oxidase inhibitor may be administered in combination with, or in conjunction with an additional therapeutic agent potentially useful in the treatment of myeloid disease, such as an inhibitor of DNA synthesis, for example: fludarabine or cladribine In some embodiments the additional therapeutic agent may be one or more agents useful in the treatment of myeloid disease, such as, but not limited to, 19yndrome19b, imetelstat, H3B-8800, eltrombopag, romiplostim, pevonedistat, 19yndrome19b, CPX-351, nivolumab, APR-246, enasidenib or ivosidenib.

In some embodiments the lysyl oxidase inhibitor may be administered in combination with, or in conjunction with an additional therapeutic agent potentially useful in the treatment of myeloid disease, such as a Jak inhibitor, for example ruxolitinib, pacritinib, fedratinib, gandotinib, lestaurtinib, or momelotinib.

In some embodiments the lysyl oxidase inhibitor may be administered in combination with, or in conjunction with an additional therapeutic agent potentially useful in the treatment of myeloid disease, such as a protein kinase inhibitor, for example sorafenib, imatinib, midostaurin or lestaurtinib.

In some embodiments the lysyl oxidase inhibitor may be administered in combination with, or in conjunction with an additional therapeutic agent potentially useful in the treatment of myeloid disease, such as a tyrosine kinase inhibitor, for example dasatinib, ponatinib, bosutinib or nilotinib.

In some embodiments the lysyl oxidase inhibitor may be administered in combination with, or in conjunction with an additional therapeutic agent potentially useful in the treatment of myeloid disease, such as a FLT inhibitor, for example quizartinib.

In some embodiments the lysyl oxidase inhibitor may be administered in combination with, or in conjunction with an additional therapeutic agent potentially useful in the treatment of myeloid disease, such as an anti-apoptosis agent, for example xIAP, cIAP1, cIAP2 or Survivin.

In some embodiments the lysyl oxidase inhibitor may be administered in combination with, or in conjunction with an additional therapeutic agent potentially useful in the treatment of myeloid disease, such as a Bcl-2 family protein inhibitor for example: venetoclax.

In some embodiments the lysyl oxidase inhibitor may be administered in combination with, or in conjunction with an additional therapeutic agent potentially useful in the treatment of myeloid disease, such as, an ALK5 inhibitor, for example, vactosertib, galunisertib or LY3200882.

In some embodiments the lysyl oxidase inhibitor may be administered in combination with, or in conjunction with an additional therapeutic agent potentially useful in the treatment of myeloid disease, such as a protein phosphatase 2A (PP2A) inhibitor, for example, okadaic acid or LB100.

In some embodiments the lysyl oxidase inhibitor may be administered in combination with, or in conjunction with an additional therapeutic agent potentially useful in the treatment of myeloid disease, such as, for example, an inhibitor of the Wnt/bcatenin signaling pathway, for example, Wnt-C59, LGK-974, X-AV-939, ICG-001, IWR-1-endo, IWR-1-exo. KY02111, IWP-2, FH535, WIK14, IWP-L6, PNU-74654, CCT036477, OMP-18R5, dimethoxy curcumin, Dickkopf, Axin, FRZB, SFRP1, and SFRP3.

In some embodiments the lysyl oxidase inhibitor may be administered in combination with, or in conjunction with an additional therapeutic agent potentially useful in the treatment of myeloid disease, such as an anti-CD47 agent, for example magrolimab In some embodiments the lysyl oxidase inhibitor may be administered in combination with, or in conjunction with an additional therapeutic agent potentially useful in the treatment of myeloid disease, such as, an inhibitor of the CD95 signaling pathway, for example asunercept.

In some embodiments the lysyl oxidase inhibitor may be administered in combination with, or in conjunction with an additional therapeutic agent potentially useful in the treatment of myeloid disease, such as a PARP inhibitor, for example: talazoparib When two or more active ingredients are co-administered, the active ingredients may be administered simultaneously, sequentially or separately. In one embodiment the LOX or LOXL inhibitor is co-administered simultaneously with one or more additional therapeutic agents. In another embodiment the LOX or LOXL inhibitor and the one or more additional therapeutic agents are administered sequentially. In a further embodiment the LOX or LOXL inhibitor and one or more additional therapeutic agents are administered separately.

In some embodiments of the methods of the present invention, the amount of the LOX or LOXL inhibitor and the amount of the additional therapeutic agent when taken together is more effective to treat the subject than when the compound or the additional therapeutic agent is administered alone. In some embodiments of the methods of the present invention, the amount of the LOX or LOXL inhibitor and the amount of the additional therapeutic agent when taken together has a greater than additive effect on the myeloid malignancy, such as MDS in the subject; i.e. the LOX or LOXL inhibitor and the additional therapeutic agent act synergistically in the treatment of the myeloid malignancy, such as MDS. In some embodiments of the methods, the amount of the LOX or LOXL inhibitor and the amount of the additional therapeutic agent when taken together is effective to reduce a clinical symptom of the myeloid malignancy, such as MDS in the subject.

A further aspect of the invention comprises a method for the treatment of myelodysplastic syndrome (MDS) in a subject, comprising administering to the subject a first composition comprising a therapeutically effective amount of a lysyl oxidase (LOX) inhibitor, a lysyl oxidase-like (LOXL) inhibitor, or a pharmaceutically acceptable salt thereof; and a second composition comprising one or more additional therapeutic agents.

In one embodiment the LOX inhibitor is the compound:

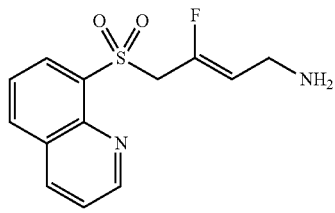 [SMILES: NC/C=C(\F)CS(=O)(=O)c1cccc2cccnc12]

and the additional therapeutic agent is 5-azacytidine. In one embodiment of the methods of the present invention the LOX inhibitor and the 5-azacytidine act synergistically in the treatment of the MDS.

In one embodiment the LOX inhibitor is the compound:

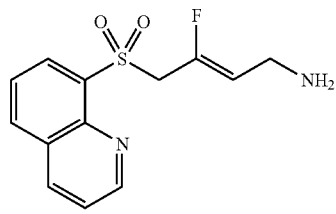 [SMILES: NC/C=C(\F)CS(=O)(=O)c1cccc2cccnc12]

and the additional therapeutic agent is decitabine. In one embodiment of the methods of the present invention the LOX inhibitor and the decitabine act synergistically in the treatment of the MDS.

In some embodiments of the methods of the present invention, the combination treatment comprises an increase in erythroid cell differentiation. In some embodiments, the increase in erythroid cell differentiation observed for the LOX or LOXL inhibitor and second therapeutic agent combination treatment is greater than the sum of the increases observed for both LOX or LOXL inhibitor treatment alone and second therapeutic agent treatment alone. In some embodiments, the LOX or LOXL inhibitor and combined with a second therapeutic agent may exhibit a synergistic effect on erythroid cell differentiation. In some embodiments of the methods of the present invention, the LOX or LOXL inhibitor alone, or in combination with one or more second therapeutic agents, may rescue erythropoiesis. In some embodiments of the methods of the present invention, the LOX or LOXL inhibitor alone, or in combination with one or more second therapeutic agents, may rescue erythropoiesis in in vitro co-cultured, patient derived, MSC/HSC cells. In some embodiments of the methods of the present invention, the LOX or LOXL inhibitor alone, or in combination with one or more second therapeutic agents, may rescue erythropoiesis in a xenotransplantation mouse model.

LOX and LOXL Inhibitors

LOX and LOXL inhibitors are known in the art and can be identified by screening compound libraries. Examples of LOX and LOXL inhibitors that can be used in the methods of the present invention include those disclosed in the following patents families: U.S. Pat. Nos. 4,454,158; 4,699,928; 4,943,593; 4,965,288; 5,021,456; 5,059,714; 5,182,297; 5,252,608; WO 2007/120528; WO 2017/141049; WO 2019/073251; WO 2019/234418; WO 2020/099886; WO 2017/136871; WO 2017/136870; WO 2018/157190; WO 2020/024017; WO 2021/012014; WO 2003/097612, WO 2006/053555; WO 2018/048930, WO 2017/139274; WO 2017/015221, WO 2017/003862, WO 2016/144702; WO 2016/144703 and US 2008/0293936. In some embodiments the lysyl oxidase inhibitor is an antibody as disclosed in US 2009/0053224 (Simtuzumab).

In some embodiments, the LOX or LOXL inhibitor is a compound as disclosed in WO 2020/024017 having the structure of Formula I:

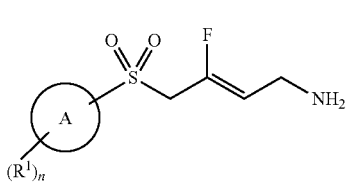

Formula I or a pharmaceutically acceptable salt, solvate, hydrate or tautomeric form thereof; wherein:

A is aryl or heteroaryl;

each $R^1$ is independently selected from the group consisting of X—$R^2$, halogen, deuterium, $C_{1-6}$alkyl, O—$C_{1-6}$ alkyl, aryl, heteroaryl, cycloalkyl, heterocycloalkyl, —CN, —C(O)O$R^3$, —C(O)N$R^4R^5$, —S(O)$_2$N$R^4R^5$, —S(O)$_2R^6$, —N$R^8$C(O)$R^9$, and —N$R^8$S(O)$_2R^9$; wherein each $C_{1-6}$alkyl, aryl, heteroaryl, cycloalkyl and heterocycloalkyl is optionally substituted by one or more substituents selected from the group consisting of halogen, —OH, —SO$_2$CH$_3$, —$C_{1-4}$alkyl, —O—$C_{1-4}$ alkyl, —CF$_3$, —CH$_2$CF$_3$ and —O—CF$_3$;

X is selected from the group consisting of O, CH$_2$, OCH$_2$, CH$_2$O, CH$_2$S(O)$_2$, CONH and NHCO;

$R^2$ is selected from the group consisting of cycloalkyl, heterocycloalkyl, aryl and heteroaryl; wherein each $R^2$ is optionally substituted by one or more $R^7$;

$R^3$ is selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —$C_{1-4}$alkyl, —O—$C_{1-4}$ alkyl, —CF$_3$, —CH$_2$CF$_3$ and —O—CF$_3$;

$R^4$ and $R^5$ are independently selected from the group consisting of hydrogen, $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —SO$_2$CH$_3$, —$C_{1-4}$alkyl, —O—$C_{1-4}$alkyl, —CF$_3$, —CH$_2$CF$_3$ and —O—CF$_3$; or $R^4$ and $R^5$ when attached to the same nitrogen atom are combined to form a 4- to 7-membered ring having from 0 to 1 additional heteroatoms as ring members;

$R^6$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$;

$R^7$ is selected from the group consisting of halogen, —OH, $C_{1-6}$alkyl, O—$C_{1-6}$alkyl $C_{3-7}$cycloalkyl, —C(O)O$R^3$, —C(O)N$R^4R^5$, —N$R^4$C(O)$R^6$, —S(O)$_2$N$R^4R^5$, —N$R^4$S(O)$_2R^6$ and —S(O)$_2R^6$; wherein each $C_{1-6}$alkyl is optionally substituted by one or more substituents selected from the group consisting of halogen and —OH;

$R^8$ is hydrogen or $C_{1-6}$alkyl;

$R^9$ is selected from the group consisting of $C_{1-6}$alkyl and $C_{3-7}$cycloalkyl; wherein each $C_{1-6}$alkyl and $C_{3-7}$cycloalkyl is optionally substituted by one or more substituents selected from the group consisting of halogen, —OH, —$C_{1-4}$alkyl, —O—$C_{1-4}$alkyl, —CF$_3$, —CH$_2$CF$_3$, and —O—CF$_3$; or $R^8$ and $R^9$ are combined to form a 5- to 7-membered ring having from 0 to 1 additional heteroatoms as ring members;

and n is 0, 1, 2, 3, 4, 5 or 6.

A, $R^1$ and n are as defined.

In one embodiment of the compounds of Formula I in WO 2020/024017, A is heteroaryl. In one embodiment, n is 0.

The compounds and methods for their preparation are disclosed in WO 2020/024017. For details, for example, on a process to manufacture, to formulate or to use this compound or a salt thereof, reference is made to this document.

In one embodiment the LOX or LOXL inhibitor is a compound disclosed in Table 2 of WO 2020/024017.

In one embodiment of the compounds disclosed in WO 2020/024017, the LOX or LOXL inhibitor is selected from and or a pharmaceutically acceptable salt thereof.

In one embodiment of the compounds disclosed in WO 2020/024017, the LOX or LOXL inhibitor is or a pharmaceutically acceptable salt thereof. This compound is Compound 33 and the synthesis is described in Example 21. This compound is also referred to as PXS-5505.

In one embodiment the LOX or LOXL inhibitor is a compound as disclosed in WO 2021/012014 of Formula I:

Formula I or a pharmaceutically acceptable salt, solvate, hydrate or tautomeric form thereof; where W, Y, Z, A, $R^1$ and n are as defined in WO 2021/012014.

The compounds and methods for their preparation are disclosed in WO 2021/012014. For details, for example, on a process to manufacture, to formulate or to use this compound or a salt thereof, reference is made to this document. In one embodiment the LOX or LOXL inhibitor is a compound disclosed in Table 2 of WO 2021/012014.

In one embodiment of the compounds disclosed in WO 2021/012014 the LOX or LOXL inhibitor is selected from the group consisting of

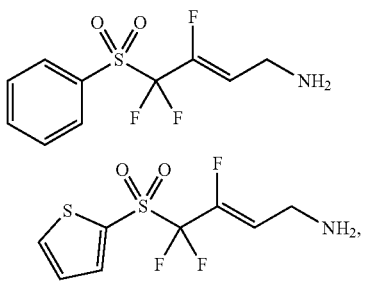

and

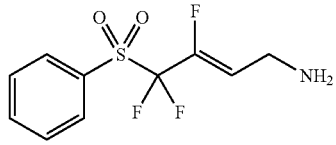 [SMILES: NC/C=C(\F)C(F)(F)S(=O)(=O)c1ccccc1]

or a pharmaceutically acceptable salt or solvate thereof. In another embodiment the LOX or LOXL inhibitor is

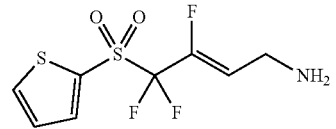 [SMILES: NC/C=C(\F)C(F)(F)S(=O)(=O)c1cccs1]

or a pharmaceutically acceptable salt or solvate thereof. In a further embodiment, the LOX or LOXL inhibitor is

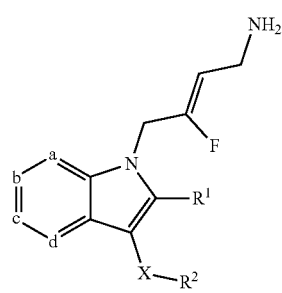

or a pharmaceutically acceptable salt or solvate thereof.

In one embodiment the LOX or LOXL inhibitor is a compound as disclosed in WO 2017/136871 of Formula I:

Formula I

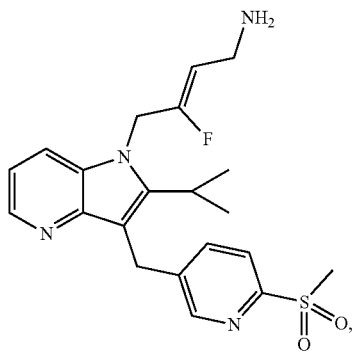 [SMILES: CC(C)c1c(Cc2ccc(S(C)(=O)=O)nc2)c2ncccc2n1C/C(F)=C/CN]

or a stereoisomer, pharmaceutically acceptable salt, polymorphic form, solvate, tautomeric form or prodrug thereof; where a, b, c, d, X, $R^1$ and $R^2$ are as defined in WO 2017/136871.

The compounds and methods for their preparation are disclosed in WO 2017/136871. For details, for example, on a process to manufacture, to formulate or to use this compound or a salt thereof, reference is made to this document. In one embodiment the LOX or LOXL inhibitor is a compound disclosed in Table 1 of WO 2017/136871.

In one embodiment of the compounds disclosed in WO 2017/136871 the LOX or LOXL inhibitor is

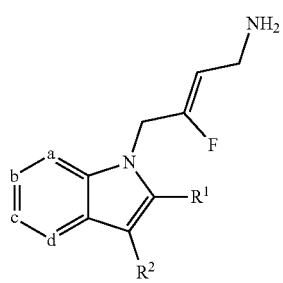

or a pharmaceutically acceptable salt thereof. This is compound 22 of WO 2017/136871.

In one embodiment the LOX or LOXL inhibitor is a compound as disclosed in WO 2017/136870 of Formula I:

Formula I

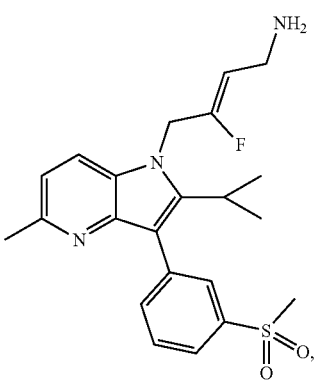 [SMILES: Cc1ccc2c(n1)c(-c1cccc(S(C)(=O)=O)c1)c(C(C)C)n2C/C(F)=C/CN]

or a stereoisomer, pharmaceutically acceptable salt, polymorphic form, solvate, tautomeric form or prodrug thereof; where a, b, c, d, $R^1$ and $R^2$ are as defined in WO 2017/136870.

The compounds and methods for their preparation are disclosed in WO 2017/136870. For details, for example, on a process to manufacture, to formulate or to use this compound or a salt thereof, reference is made to this document. In one embodiment the LOX or LOXL inhibitor is a compound disclosed in Table 1 of WO 2017/136870.

In one embodiment of the compounds disclosed in WO 2017/136870 the LOX or LOXL inhibitor is or a pharmaceutically acceptable salt thereof. This is compound 112 of WO 2017/136870.

In some embodiments, the LOX or LOXL inhibitor is a compound as disclosed in WO 2018/157190 of Formula I:

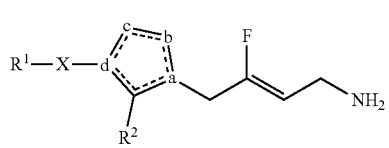

Formula I

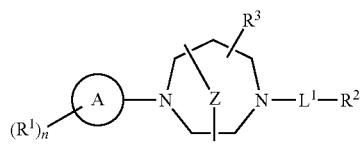
(I)

or a stereoisomer, pharmaceutically acceptable salt, polymorphic form, solvate, tautomeric form or prodrug thereof; where each ⁓ is independently a single or double bond arranged so as to provide a pyrazole ring and a, b, c, d, X, $R^1$ and $R^2$ are as defined in WO 2018/157190.

The compounds and methods for their preparation are disclosed in WO 2018/157190. For details, for example, on a process to manufacture, to formulate or to use this compound or a salt thereof, reference is made to this document. In one embodiment the LOX or LOXL inhibitor is a compound disclosed in Table 1 of WO 2018/157190.

In some embodiments the LOX or LOXL inhibitor is a compound as disclosed in WO 2020/099886 of Formula I:

Formula (I)

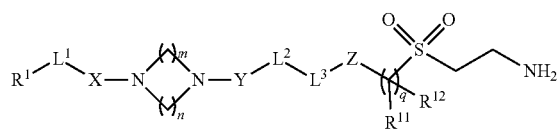

or a pharmaceutically acceptable salt thereof wherein X, Y, $R^1$, $R^{11}$, $R^{12}$, $L^1$, $L^2$, $L^3$, m, n and q are as defined in WO 2020/099886.

The compounds and methods for their preparation are disclosed in WO 2020/099886. For details, for example, on a process to manufacture, to formulate or to use this compound or a salt thereof, reference is made to this document. In one embodiment the LOX or LOXL inhibitor is a compound disclosed in claim 22 or 23 of WO 2020/099886.

In some embodiments the LOX or LOXL inhibitor is a compound as disclosed in WO 2019/234418 of Formula I:

Formula (I)

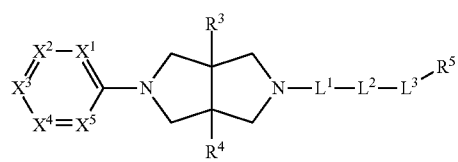

or a pharmaceutically acceptable salt thereof wherein $X^1$, $X^2$, $X^3$, $X^4$, $X^5$, $R^3$, $R^4$, $R^5$, $L^1$, $L^2$ and $L^3$ are as defined in WO 2019/234418.

The compounds and methods for their preparation are disclosed in WO 2019/234418. For details, for example, on a process to manufacture, to formulate or to use this compound or a salt thereof, reference is made to this document. In one embodiment the LOX or LOXL inhibitor is a compound disclosed in claim 18 of WO 2019/234418.

In some embodiments the LOX or LOXL inhibitor is a compound as disclosed in WO 2019/073251 of Formula I:

or a pharmaceutically acceptable salt thereof wherein A, Z, $R^1$, $R^2$, $R^3$ and n are as defined in WO 2019/073251.

The compounds and methods for their preparation are disclosed in WO 2019/073251. For details, for example, on a process to manufacture, to formulate or to use this compound or a salt thereof, reference is made to this document. In one embodiment the LOX or LOXL inhibitor is a compound disclosed in claim 15 of WO 2019/073251.

In some embodiments the LOX or LOXL inhibitor is a compound as disclosed in WO 2017/141049 of Formula I:

(I)

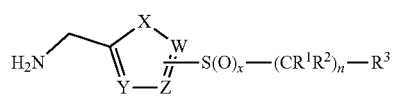

or a pharmaceutically acceptable salt thereof, wherein W, X, Y, Z, $R^1$, $R^2$, $R^3$, n and x are as defined in WO 2017/141049.

The compounds and methods for their preparation are disclosed in WO 2017/141049. For details, for example, on a process to manufacture, to formulate or to use this compound or a salt thereof, reference is made to this document.

In some embodiments the LOX or LOXL inhibitor is a compound as disclosed in WO 2018/048930 of Formula I:

Formula (I)

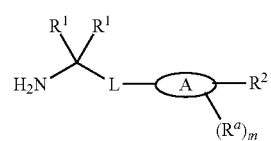

or a pharmaceutically acceptable salt or solvate thereof, wherein A, L, $R^1$, $R^2$, $R^8$ and m are as defined in WO 2018/048930.

The compounds and methods for their preparation are disclosed in WO 2018/048930. For details, for example, on a process to manufacture, to formulate or to use this compound or a salt thereof, reference is made to this document. In one embodiment the LOX or LOXL inhibitor is a compound disclosed in claim 74 of WO 2018/048930.

In some embodiments the LOX or LOXL inhibitor is a compound as disclosed in WO 2017/139274 of Formula I:

Formula (I)

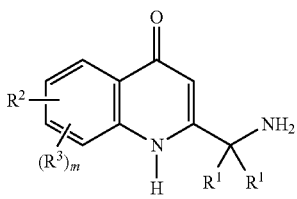

or a pharmaceutically acceptable salt or solvate thereof, wherein $R^1$, $R^2$, $R^3$ and m are as defined in WO 2017/139274.

The compounds and methods for their preparation are disclosed in WO 2017/139274. For details, for example, on a process to manufacture, to formulate or to use this compound or a salt thereof, reference is made to this document. In one embodiment the LOX or LOXL inhibitor is a compound disclosed in claim 35 of WO 2017/139274.

In some embodiments the LOX or LOXL inhibitor is a compound as disclosed in WO 2017/015221 of Formula I:

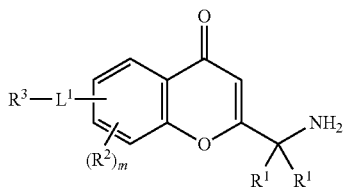

Formula (I)

or a pharmaceutically acceptable salt or solvate thereof, wherein $L^1$, $R^1$, $R^2$, $R^3$ and m are as defined in WO 2017/015221.

The compounds and methods for their preparation are disclosed in WO 2017/015221. For details, for example, on a process to manufacture, to formulate or to use this compound or a salt thereof, reference is made to this document. In one embodiment the LOX or LOXL inhibitor is a compound disclosed in claim 24 of WO 2017/015221.

In some embodiments the LOX or LOXL inhibitor is a compound as disclosed in WO 2017/003862 of Formula I:

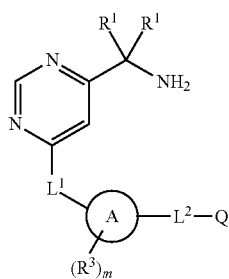

Formula (I)

or a pharmaceutically acceptable salt or solvate thereof, wherein $L^1$, $L^2$, Q, A, $R^1$, $R^3$ and m are as defined in WO 2017/003862.

The compounds and methods for their preparation are disclosed in WO 2017/003862. For details, for example, on a process to manufacture, to formulate or to use this compound or a salt thereof, reference is made to this document. In one embodiment the LOX or LOXL inhibitor is a compound disclosed in Table 1 or claim 48 of WO 2017/003862.

In some embodiments the LOX or LOXL inhibitor is a compound as disclosed in WO 2016/144702 of Formula VI:

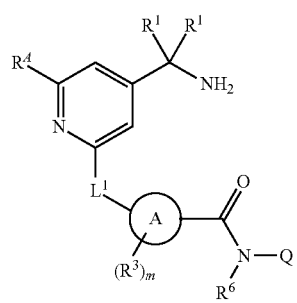

Formula (VI)

or a pharmaceutically acceptable salt thereof, wherein $L^1$, Q, A, $R^1$, $R^3$, $R^4$, $R^6$ and m are as defined in WO 2016/144702.

The compounds and methods for their preparation are disclosed in WO 2016/144702. For details, for example, on a process to manufacture, to formulate or to use this compound or a salt thereof, reference is made to this document. In one embodiment the LOX or LOXL inhibitor is a compound disclosed in claim 33 of WO 2016/144702.

In some embodiments the LOX or LOXL inhibitor is a compound as disclosed in WO 2016/144703 of Formula I:

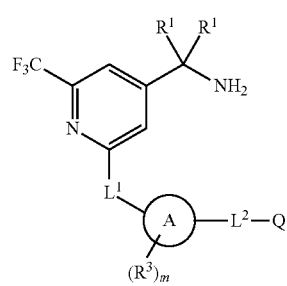

Formula (I)

or a pharmaceutically acceptable salt thereof, wherein $L^1$, $L^2$, Q, A, $R^1$, $R^3$ and m are as defined in WO 2016/144703.

The compounds and methods for their preparation are disclosed in WO 2016/144703. For details, for example, on a process to manufacture, to formulate or to use this compound or a salt thereof, reference is made to this document. In one embodiment the LOX or LOXL inhibitor is a compound disclosed in claim 44 of WO 2016/144703.

Preparation of LOX and LOXL Inhibitors

LOX and LOXL inhibitors can be readily prepared by those skilled in the art using methods and materials known in the art and with reference to standard textbooks, such as "Advanced Organic Chemistry" by Jerry March (third edition, 1985, John Wiley and Sons) or "Comprehensive Organic Transformations" by Richard C. Larock (1989, VCH Publishers).

LOX and LOXL inhibitors that can be used in the methods of the present invention can be prepared according to methods disclosed in the following patents families. U.S. Pat. Nos. 4,454,158; 4,699,928; 4,943,593; 4,965,288; 5,021,456; 5,059,714; 5,182,297; 5,252,608; WO 2007/120528; WO 2017/141049; WO 2019/073251; WO 2019/234418; WO 2020/099886; WO 2017/136871; WO 2017/136870; WO 2018/157190; WO 2020/024017; WO 2021/012014; WO 2003/097612; WO 2006/053555; WO 2018/048930, WO 2017/139274; WO 2017/015221, WO 2017/003862, WO 2016/144702; WO 2016/144703 and US 2008/0293936.

Pharmaceutical and/or Therapeutic Formulations

In another embodiment of the present invention, there are provided compositions comprising a LOX or LOXL inhibitor and at least one pharmaceutically acceptable excipient, carrier or diluent thereof for use in the treatment of MDS. The LOX or LOXL inhibitor may also be present as suitable salts, including pharmaceutically acceptable salts.

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

The phrase "pharmaceutically acceptable salt" refers to any salt preparation that is appropriate for use in a pharmaceutical application. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art and include acid addition and base salts. Hemisalts of acids and bases may also be formed. Pharmaceutically acceptable salts include amine salts of mineral acids (e.g., hydrochlorides, hydrobromides, sulfates, and the like); and amine salts of organic acids (e.g., formates, acetates, lactates, malates, tartrates, citrates, ascorbates, succinates, maleates, butyrates, valerates, fumarates, sulfonates and the like).

Compositions herein comprise one or more compounds provided herein. The compounds are, in one embodiment, formulated into suitable pharmaceutical preparations such as solutions, suspensions, tablets, creams, gels, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein, and then extrapolated from there for dosages for humans.

The concentration of active compound in the pharmaceutical composition will depend on absorption, distribution, inactivation and elimination rates of the active compound, the physicochemical characteristics of the compound, the dosage schedule, and amount administered as well as other factors known to those of skill in the art.

Dosing may occur at intervals of minutes, hours, days, weeks, months or years or continuously over any one of these periods. Suitable dosages lie within the range of about 0.1 ng per kg of body weight to 0.1 g per kg of body weight per dosage. The dosage is preferably in the range of 1 µg to 0.1 g per kg of body weight per dosage, such as is in the range of 1 mg to 0.1 g per kg of body weight per dosage. Suitably, the dosage is in the range of 1 µg to 50 mg per kg of body weight per dosage, such as 1 µg to 20 mg per kg of body weight per dosage, or 1 µg to 10 mg per kg of body weight per dosage. Other suitable dosages may be in the range of 1 mg to 25 mg per kg of body weight, including 1 mg to 10, 20, 50 or 100 mg per kg of body weight per dosage or 10 µg to 100 mg per kg of body weight per dosage. In one embodiment, the dosage is in the range of 1 mg to 10 mg per kg of body weight per dosage.

Suitable dosage amounts and dosing regimens can be determined by the attending physician and may depend on the particular condition being treated, the severity of the condition, as well as the general health, age and weight of the subject.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof.

The pharmaceutically therapeutically active compounds and derivatives thereof are, in one embodiment, formulated and administered in unit-dosage forms or multiple-dosage forms. The active ingredient may be administered at once, or may be divided into a number of smaller doses to be administered at intervals of time. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules. Hence, multiple dose form is a multiple of unit-doses which are not segregated in packaging.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %) and in another embodiment 0.1-25%. (wt %) active ingredient. The amount of active in such therapeutically useful compositions is such that an effective dosage level can be attained.

Modes of Administration

Convenient modes of administration include injection (subcutaneous, intravenous, etc.), oral administration, inhalation, transdermal application, topical to skin, eyes, ears, oral surfaces, vaginal or rectal administration. Depending on the route of administration, the formulation and/or compound may be coated with a material to protect the compound from the action of enzymes, acids and other natural conditions which may inactivate the therapeutic activity of the compound. The compound may also be administered parenterally or intraperitoneally.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a colouring agent; a sweetening agent; a flavouring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and ethanol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

Injectables, Solutions and Emulsions

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, olive oil, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intra-arterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Compositions for Other Routes of Administration

Of interest herein are also lyophilized powders, which can be reconstituted for administration as solutions, emulsions and other mixtures. They may also be reconstituted and formulated as solids or gels.

Other routes of administration, such as topical administration, transdermal patches, including iontophoretic and electrophoretic devices, vaginal and rectal administration, are also contemplated herein.

The invention will now be described in greater detail, by way of illustration only, with reference to the following non-limiting examples. The examples are intended to serve to illustrate the invention and should not be construed as limiting the generality of the disclosure of the description throughout this specification.

Example 1

Isolation and Culture of Primary Human and Mouse CD34+ Cells from Bone Marrow Aspirates Healthy CD34+ cells were isolated from hip replacement surgery bone specimen (old CD34+ cells) or collected by iliac crest puncture of healthy volunteers (young CD34+ cells). Approval for collection of patient samples was given by the Institutional Review Board of the Medical Faculty Mannheim, University of Heidelberg, Germany, in accordance with the declaration of Helsinki. All patients were informed and provided written consent for sample collection. Mononuclear cells (MNC) were isolated from bone marrow by Ficoll density gradient. CD34+ cells from MNC were isolated using MACS enrichment columns (Miltenyi Biotec, Bergisch Gladbach, Germany) according to the manufacturer's instructions as described [18]. Purity of the CD34+ populations were confirmed by FACS analysis to be >95%. These were then viably frozen and thawed immediately before xenotransplantation.

Mesenchymal Stromal Cell Isolation and Erythroid Differentiation

Figure 1:
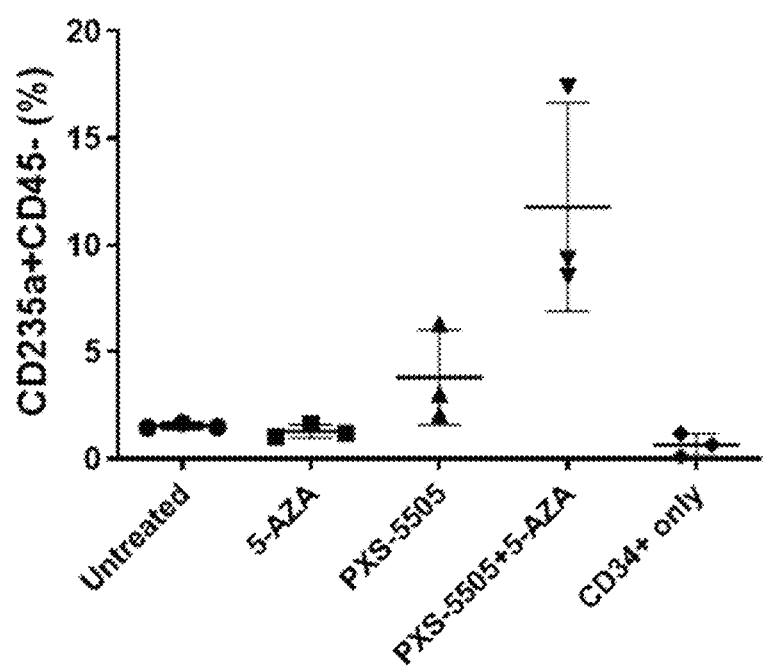
FIG. 1 depicts erythroid differentiation (n=3) in in vitro co-cultured, patient derived, MSC/HSC cells. There is a synergistic increase in erythroid differentiation when treated with both 5-azacytidine (5-AZA; 100 nM) and PXS-5505 (2 μM).

Mesenchymal stromal cells (MSC) were isolated from residual diagnostic material and selected via their plastic adherence properties in culture. MSC were expanded in NH-Expansion medium (Miltenyi Biotec) and cultured to a maximum of 4 passages. Ex-vivo expanded MSCs were FACS analyzed to confirm adherence to the minimal criteria for defining multipotent mesenchymal stromal cells as described in [Medyouf, 2014]. Patient MDS cultures were treated daily with or without 2 µM of PXS-5505 for 6 consecutive days then co-cultured with autologous CD34+ cells for 4 days. The co-cultured cells were in a 6 well plate in serum free medium (StemSpan, Stem Cell Technologies, Vancouver, Canada) supplemented with IL-3 at 10 ng/mL, IL-6 at 10 ng/mL, SCF at 50 ng/mL, TPO at 25 ng/mL and Flt3L 50 ng/mL (Peprotech, Rocky Hill, NJ). Co-cultured cells were treated daily with 2 µM PXS-5505, 100 nM 5-azacytidine (5-AZA) or left untreated. CD34+ cells were seeded on MethoCult™ H4435 Enriched Methylcellulose-based medium (Stemcell Technologies) and analyzed for erythroid differentiation (CD235a$^+$, CD45− cells as used in Mossner, 2016 [19] by flow cytometry after 14 days. The synthesis of PXS-5505 is described in Example 21 of WO 2020/024017. FIG. 1 depicts the proportion of the patient MSC/HSC co-culture cells that have undergone erythroid differentiation. The combination treatment of PXS-5505 and 5-AZA significantly increased erythroid cell differentiation. Furthermore, the results demonstrate that the increase in erythroid cell differentiation observed for 5-AZA and PXS-5505 combination treatment is greater than the sum of the increases observed for both 5-AZA treatment and PXS-5505 treatment alone. That is to say, 5-AZA combined with PXS-5505 exhibited a synergistic effect on erythroid cell differentiation. These results demonstrate that PXS-5505 alone, or in combination with 5-AZA, could rescue erythropoiesis in in vitro co-cultured, patient derived, MSC/HSC cells. CD34+ cells cultured alone had minimal differentiated erythroid cells.

Example 2

Xenotransplantation Implantation and Erythroid Differentiation

Figure 2:
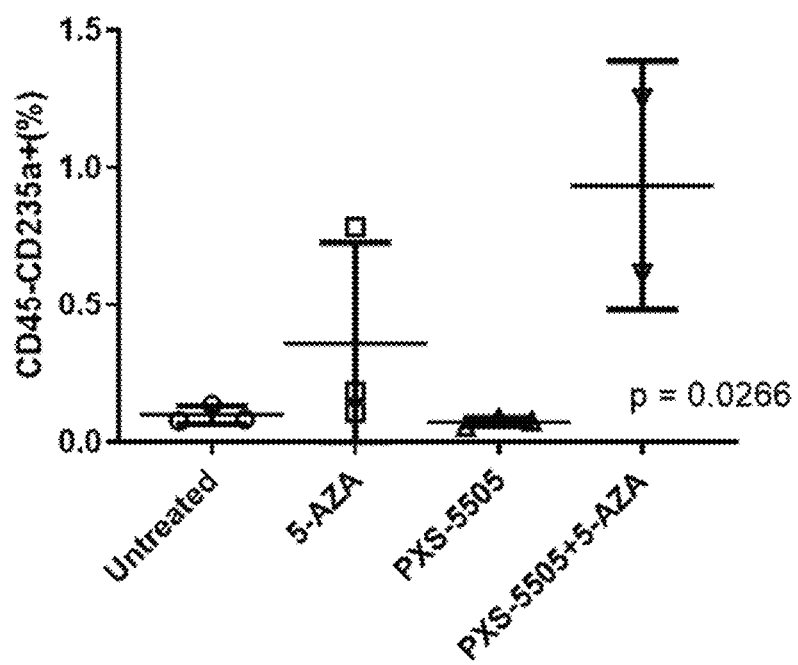
FIG. 2 shows that the combination treatment with PXS-5505 and 5-AZA synergistically increased the erythroid differentiation (the CD235a$^+$ and CD45– population) in the bone marrow collected from xenotransplanted mice.

Female immunocompromised mice (NSG and NSGS, Jackson Laboratory) aged 6-8 week old were sub-lethally irradiated (200 cGy) before intrafemoral injections with a mix of CD34+ and MSCs cells ($1 \times 10^5 : 5 \times 10^5$) from primary myelofibrosis patients (with grade 3 fibrosis) as described previously [Medyouf, 2014]. The mice were treated with 5-AZA (75 mg/m² 5+2 schedule, 3 cycles in total) and/or PXS-5505 (30 mg/kg every 48 h for the duration of 5-AZA treatment) for 3 months. At endpoint human CD45+ cells were FACS-sorted from mouse bone marrow. The CD45+ cells were differentiated in the medium supplemented with 5 U/mL EPO, 100 ng/mL SCF and 5 ng/mL IL-3 for 21 days followed by flow cytometry analysis for CD235a and CD45 markers as described previously [18]. FIG. 2 shows that the combination treatment with PXS-5505 and 5-AZA synergistically increased the erythroid differentiation (the CD235a$^+$ and CD45− population) in the bone marrow collected from xenotransplanted mice. Furthermore, the results demonstrate that the increase in erythroid cell differentiation observed for 5-AZA and PXS-5505 combination treatment is greater than the sum of the increases observed for both 5-AZA treatment and PXS-5505 treatment alone. That is to say, 5-AZA combined with PXS-5505 exhibited a synergistic effect on erythroid cell differentiation. These results demonstrate that PXS-5505 alone, or in combination with 5-AZA, could rescue erythropoiesis in a xenotransplantation mouse model.

Table 1 shows the ratios of in vivo erythroid differentiation in mice treated with the combination treatment (PXS-5505 and 5-AZA) over the 5-AZA treatment alone (rescue erythroid differentiation ratio). Furthermore, it presents the rescue erythroid differentiation for a variety of different disease subtypes of myelodysplastic syndrome, chronic myelomonocytic leukemia and acute myeloid leukemia. These results demonstrate that the combination of PXS-5505 and 5-AZA is effective for erythropoiesis rescue across different diseases.

TABLE 1

Subtypes of myeloid malignancies with a ratio of the rescue of erythroid differentiation from the bone marrow of the xenotransplanted mice that received the combination treatment (PXS-5505 and 5-AZA) over those treated with 5-AZA alone.

| Myeloid Disease | Ratio CD235 + CD45 cells; PXS5505 + 5-AZA/5-AZA |
| --- | --- |
| Myelodysplastic syndrome - Metachromatic leukodystrophy | 1.6 |
| Chronic myelomonocytic leukemia | 2.1 |
| Myelodysplastic syndrome - Ring sideroblasts - Single lineage dysplasia | 2.2 |
| Myelodysplastic syndrome - Excess blasts | 18.2 |
| Secondary acute myeloid leukemia | 5.3 |
| Myelodysplastic syndrome | 9.2 |
| Myelodysplastic syndrome - Refractory anaemia with ring sideroblasts | 1.3 |
| Myelodysplastic syndrome - Ring sideroblasts - Metachromatic leukodystrophy | 1.4 |
| Myelodysplastic syndrome - del5q | 5.2 |
| Myelodysplastic syndrome - Myeloproliferative neoplasm | 1.5 |

The mouse spleens were also collected and spleen index calculated as follows: spleen index (%)=spleen weight/body weight×100. FIG. 3 shows the spleen index in mice treated with a combination of PXS-5505 and 5-AZA. The spleen index was reduced with the combination treatment (5-AZA and PXS-5505) (FIG. 3). The single treatments of 5-AZA and PXS-5505 had a similar trend of reducing the spleen index.

Example 3

Quantitative RT PCR

Bone marrow aspirate samples were collected from myelodysplastic syndrome (MDS) patients and healthy subjects via iliac crest puncture according to previously described protocols [20]. Approval for collection of patient samples was given by the Institutional Review Board of the Medical Faculty Mannheim, University of Heidelberg, Germany, in accordance with the declaration of Helsinki. All patients were informed and provided written consent for sample collection.

RNA was extracted and cDNA synthetized as per previously described protocols [Schilter, 2018]. Quantitative real-time PCR was performed using validated human probe sets for LOX, LOXL1, LOXL2, LOXL3 and LOXL4 as previously described by Shilter et al [21]. Relative mRNA expression levels for each transcript of interest were normalized to GAPDH and then quantified using the comparative double CT method for each biological replicate. Results, depicted in FIG. 4, show that MDS patients had an increased LOX, LOXL2 and LOXL3 and LOXL4 expression when compared to healthy subjects. Only LOXL1 expression was unchanged between healthy and MDS patients.

Example 4

Measurement of LOXL2 Concentration and Enzyme Activity in Patient Samples Using the Simoa™ Assay LOXL2 concentration and/or activity assays use a Simoa HD-analyzer (Quanterix Corporation) and Single Molecule Array (Simoa™) technology to measure total LOXL2 and LOXL2 activity in bone marrow aspirate samples. The Simoa™ technology has been previously described by Rissin, 2010 [22].

A bioprobe of the following structure was utilized in this assay:

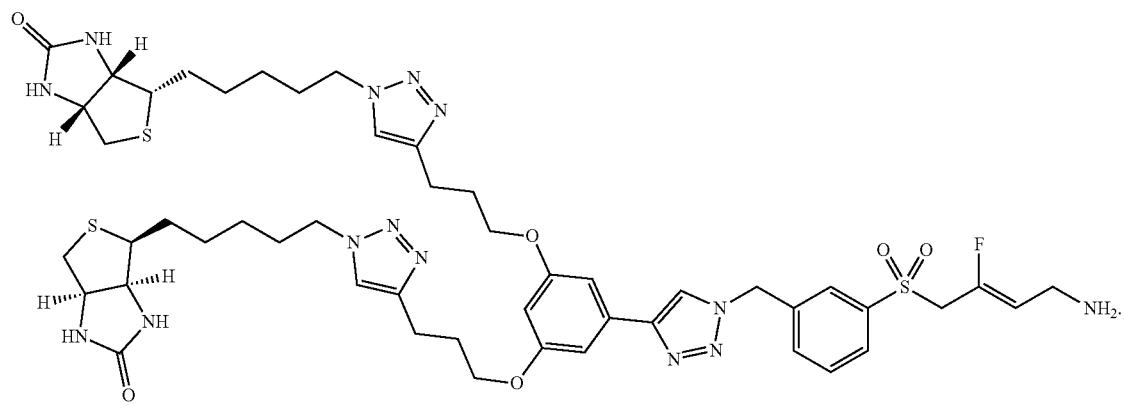 [SMILES: NC/C=C(\F)CS(=O)(=O)c1cccc(Cn2cc(-c3cc(OCCCc4cn(CCCCC[C@@H]5SC[C@@H]6NC(=O)N[C@@H]65)nn4)cc(OCCCc4cn(CCCCC[C@@H]5SC[C@@H]6NC(=O)N[C@@H]65)nn4)c3)nn2)c1]

This bioprobe is compound 1-12 from PCT/AU2021/050092. Methods for the preparation of this bioprobe are described in PCT/AU2021/050092.

Paramagnetic capture beads were coated with a LOXL2 capture antibody (R&D systems, AF2639). 100 μL of pre-diluted sample (4-fold for LOXL2) in buffer (0.5% Casein, 0.25% Tween-20 in PBS) was combined in a cuvette with the capture beads (25 μL for protein content at $1.6 \times 10^7$ beads/mL; 100 μL for enzyme activity at $4 \times 10^6$ beads/mL). The biotinylated detector agent (for protein content: AB213598 LOXL2 detection antibody; for enzyme activity: bioprobe was added during the same incubation with intermittent shaking, at room temperature (35 minutes for protein content or 54 minutes for enzyme activity).

LOXL2 in the sample was captured by the antibody coated beads and bound with the detector agent simultaneously. After incubation, beads were pelleted by magnetic separation, excess sample/buffer and reagents were aspirated off, and beads were re-suspended in wash buffer to remove unbound proteins and excess reagents.

Following LOXL2 capture and incubation with the detector, a conjugate of streptavidin-β-galactosidase (SβG; 100 μL at 350 μM) was mixed with the beads and incubated (5 minutes with intermittent shaking at room temperature). SβG bound to the biotinylated detector agent and resulted in enzyme-labelling of captured LOXL2. Following a final wash, the beads were suspended in a resorufin-β-D-galactopyranoside (RGP) substrate solution and transferred to a Simoa™ Disc (containing a microarray to separate beads into individual microwells). After settling into the microarray via gravity, beads were then sealed in microwells with oil. If LOXL2 was captured and labelled on the bead, β-galactosidase hydrolyzed the RGP substrate in the microwell into a fluorescent product that provided the signal for measurement. A single-labelled target molecule resulted in sufficient fluorescent signal in 30 seconds that could be detected and counted by the Simoa™ optical system. The percentage of bead-containing wells in the array that had a positive signal was proportional to the amount of target or activity present in the sample.

To determine protein concentration, data was interpolated from a calibration curve. For enzyme activity, samples were incubated for at least 30 minutes at room temperature with or without the pan-LOX inhibitor (100 μM BAPN). Data was presented as the ratio between the signal obtained in the presence of the pan-LOX inhibitor (BAPN low signal control) and in the absence of the inhibitor (high signal control). The activity unit was presented as a signal to noise (S/N ratio) and is considered to be the specific LOXL2 activity in the sample. All samples were measured in triplicate and the mean was presented per sample. The values were excluded if the means was greater than 2 standard deviations from the mean. FIG. 5 shows that bone marrow aspirates from MDS patients with a high fibrosis grade also had a significant increase in LOXL2 concentration compared to healthy subjects. That is to say, the LOXL2 concentration in the bone marrow aspirates significantly increased with increase in severity of the MDS patient fibrosis grade. FIG. 6 depicts data from the same MDS patient samples used in the LOXL2 concentration assay: the LOXL2 activity, as measured by the Simoa™ assay, in the bone marrow aspirates also increased with increase in severity of the MDS patient fibrosis grade.

REFERENCES

[1] N. Cancer Genome Atlas Research, T. J. Ley, C. Miller, L. Ding, B. J. Raphael, A. J. Mungall, A. Robertson, K. Hoadley, T. J. Triche, Jr., P. W. Laird, J. D. Baty, L. L. Fulton, R. Fulton, S. E. Heath, J. Kalicki-Veizer, C. Kandoth, J. M. Klco, D. C. Koboldt, K. L. Kanchi, S. Kulkarni, T. L. Lamprecht, D. E. Larson, L. Lin, C. Lu, M. D. McLellan, J. F. McMichael, J. Payton, H. Schmidt, D. H. Spencer, M. H. Tomasson, J. W. Wallis, L. D. Wartman, M. A. Watson, J. Welch, M. C. Wendl, A. Ally, M. Balasundaram, I. Birol, Y. Butterfield, R. Chiu, A. Chu, E. Chuah, H. J. Chun, R. Corbett, N. Dhalla, R. Guin, A. He, C. Hirst, M. Hirst, R. A. Holt, S. Jones, A. Karsan, D. Lee, H. I. Li, M. A. Marra, M. Mayo, R. A. Moore, K. Mungall, J. Parker, E. Pleasance, P. Plettner, J. Schein, D. Stoll, L. Swanson, A. Tam, N. Thiessen, R. Varhol, N. Wye, Y. Zhao, S. Gabriel, G. Getz, C. Sougnez, L. Zou, M. D. Leiserson, F. Vandin, H. T. Wu, F. Applebaum, S. B. Baylin, R. Akbani, B. M. Broom, K. Chen, T. C. Motter, K. Nguyen, J. N. Weinstein, N. Zhang, M. L. Ferguson, C.

Adams, A. Black, J. Bowen, J. Gastier-Foster, T. Grossman, T. Lichtenberg, L. Wise, T. Davidsen, J. A. Demchok, K. R. Shaw, M. Sheth, H. J. Sofia, L. Yang, J. R. Downing, G. Eley, Genomic and epigenomic landscapes of adult de novo acute myeloid leukemia, N Engl J Med, 368 (2013) 2059-2074.

[2] M. Cazzola, D. L. Longo, Myelodysplastic Syndromes, New England Journal of Medicine, 383 (2020) 1358-1374.

[3] X. Ma, Epidemiology of myelodysplastic syndromes, Am J Med, 125 (2012) S2-5.

[4] M. Bessler, D. B. Wilson, P. J. Mason, Dyskeratosis congenita, FEBS Lett, 584 (2010) 3831-3838.

[5] Y. Kee, A. D. D'Andrea, Molecular pathogenesis and clinical management of Fanconi anemia, J Clin Invest, 122 (2012) 3799-3806.

[6] P. Greenberg, C. Cox, M. M. LeBeau, P. Fenaux, P. Morel, G. Sanz, M. Sanz, T. Vallespi, T. Hamblin, D. Oscier, K. Ohyashiki, K. Toyama, C. Aul, G. Mufti, J. Bennett, International Scoring System for Evaluating Prognosis in Myelodysplastic Syndromes, Blood, 89 (1997) 2079-2088.

[7] G. Damaj, A. Duhamel, M. Robin, Y. Beguin, M. Michallet, M. Mohty, S. Vigouroux, P. Bories, A. Garnier, J. El Cheikh, C. E. Bulabois, A. Huynh, J. O. Bay, F. Legrand, E. Deconinck, N. Fegueux, L. Clement, C. Dauriac, N. Maillard, J. Comillon, L. Ades, G. Guillerm, A. Schmidt-Tanguy, Z. Marjanovic, S. Park, M. T. Rubio, J. P. Marolleau, F. Garnier, I. Fenaux, I. Yakoub-Agha, Impact of azacitidine before allogeneic stem-cell transplantation for myelodysplastic syndromes: a study by the Societe Francaise de Greffe de Moelle et de Therapie-Cellulaire and the Groupe-Francophone des Myelodysplasies, J Clin Oncol, 30 (2012) 4533-4540.

[8] F. R. Appelbaum, J. Anderson, Allogeneic bone marrow transplantation for myelodysplastic syndrome: outcomes analysis according to IPSS score, Leukemia, 12 Suppl 1 (1998) S25-29.

[9] R. Martino, S. Iacobelli, R. Brand, T. Jansen, A. van Biezen, J. Finke, A. Bacigalupo, D. Beelen, J. Reiffers, A. Devergie, E. Alessandrino, G. J. Mufti, R. Barge, J. Sierra, T. Ruutu, M. Boogaerts, M. Falda, J. P. Jouet, D. Niederwieser, T. de Witte, B. Myelodysplastic Syndrome subcommittee of the Chronic Leukemia Working Party of the European, G. Marrow Transplantation, Retrospective comparison of reduced-intensity conditioning and conventional high-dose conditioning for allogeneic hematopoietic stem cell transplantation using HLA-identical sibling donors in myelodysplastic syndromes, Blood, 108 (2006) 836-846.

[10] C. S. Cutler, S. J. Lee, P. Greenberg, H. J. Deeg, W. S. Perez, C. Anasetti, B. J. Bolwell, M. S. Cairo, R. P. Gale, J. P. Klein, H. M. Lazarus, J. L. Liesveld, P. L. McCarthy, G. A. Milone, J. D. Rizzo, K. R. Schultz, M. E. Trigg, A. Keating, D. J. Weisdorf, J. H. Antin, M. M. Horowitz, A decision analysis of allogeneic bone marrow transplantation for the myelodysplastic syndromes: delayed transplantation for low-risk myelodysplasia is associated with improved outcome, Blood, 104 (2004) 579-585.

[11] J. Sierra, W. S. Perez, C. Rozman, E. Carreras, J. P. Klein, J. D. Rizzo, S. M. Davies, H. M. Lazarus, C. N. Bredeson, D. I. Marks, C. Canals, M. A. Boogaerts, J. Goldman, R. E. Champlin, A. Keating, D. J. Weisdorf, T. M. de Witte, M. M. Horowitz, Bone marrow transplantation from HLA-identical siblings as treatment for myelodysplasia, Blood, 100 (2002) 1997-2004.

[12] E. M. Sloand, C. O. Wu, P. Greenberg, N. Young, J. Barrett, Factors affecting response and survival in patients with myelodysplasia treated with immunosuppressive therapy, J Clin Oncol, 26 (2008) 2505-2511.

[13] P. Fenaux, G. J. Mufti, E. Hellstrom-Lindberg, V. Santini, C. Finelli, A. Giagounidis, R. Schoch, N. Gattermann, G. Sanz, A. List, S. D. Gore, J. F. Seymour, J. M. Bennett, J. Byrd, J. Backstrom, L. Zimmerman, D. McKenzie, C. L. Beach, L. R. Silverman, Efficacy of azacitidine compared with that of conventional care regimens in the treatment of higher-risk myelodysplastic syndromes: a randomised, open-label, phase III study, The Lancet Oncology, 10 (2009) 223-232.

[14] T. de Witte, S. Suciu, G. Verhoef, B. Labar, E. Archimbaud, C. Aul, D. Selleslag, A. Ferrant, P. Wijermans, F. Mandelli, S. Amadori, U. Jehn, P. Muus, M. Boogaerts, R. Zittoun, A. Gratwohl, H. Zwierzina, A. Hagemeijer, R. Willemze, Intensive chemotherapy followed by allogeneic or autologous stem cell transplantation for patients with myelodysplastic syndromes (MDSs) and acute myeloid leukemia following MDS, Blood, 98 (2001) 2326-2331.

[15] J. L. Spivak, Myeloproliferative Neoplasms, N Engl J Med, 376 (2017) 2168-2181.

[16] T. N. Tanaka, R. Bejar, MDS overlap disorders and diagnostic boundaries, Blood, 133 (2019) 1086-1095.

[17] W. Chen, A. Yang, J. Jia, Y. V. Popov, D. Schuppan, H. You, Lysyl oxidase (LOX) family members: rationale and their potential as therapeutic targets for liver fibrosis, Hepatology, 72 (2020) 729-741.

[18] H. Medyouf, M. Mossner, J. C. Jann, F. Nolte, S. Raffel, C. Herrmann, A. Lier, C. Eisen, V. Nowak, B. Zens, K. Mudder, C. Klein, J. Oblander, S. Fey, J. Vogler, A. Fabarius, E. Riedl, H. Roehl, A. Kohlmann, M. Staller, C. Haferlach, N. Muller, T. John, U. Platzbecker, G. Metzgeroth, W. K. Hofinann, A. Trumpp, D. Nowak, Myelodysplastic cells in patients reprogram mesenchymal stromal cells to establish a transplantable stem cell niche disease unit, Cell Stem Cell, 14 (2014) 824-837.

[19] M. Mossner, J. C. Jann, J. Wittig, F. Nolte, S. Fey, V. Nowak, J. Oblander, J. Pressler, I. Palme, C. Xanthopoulos, T. Boch, G. Metzgeroth, H. Rohl, S. H. Witt, H. Dukal, C. Klein, S. Schmitt, P. Gelss, U. Platzbecker, E. Balaian, A. Fabarius, H. Blum, T. J. Schulze, M. Meggendorfer, C. Haferlach, A. Trumpp, W. K. Hofinann, H. Medyouf, D. Nowak, Mutational hierarchies in myelodysplastic syndromes dynamically adapt and evolve upon therapy response and failure, Blood, 128 (2016) 1246-1259.

[20] S. Gueller, M. Komor, D. Nowak, C. D. Baldus, S. de Vos, D. Hoelzer, O. G. Ottmann, W. K. Hofinann, Identification of defects in the transcriptional program during lineage-specific in vitro differentiation of CD34(+) cells selected from patients with both low- and high-risk myelodysplastic syndrome, Exp Hematol, 38 (2010) 718-732, 732 e711-716.

[21] H. Schilter, A. D. Findlay, L. Perryman, T. T. Yow, J. Moses, A. Zahoor, C. I. Turner, M. Deodhar, J. S. Foot, W. Zhou, A. Greco, A. Joshi, B. Rayner, S. Townsend, A. Buson, W. Jarolimek, The lysyl oxidase like 2/3 enzymatic inhibitor, PXS-5153A, reduces crosslinks and ameliorates fibrosis, J Cell Mol Med, 23 (2019) 1759-1770.

[22] D. M. Rissin, C. W. Kan, T. G. Campbell, S. C. Howes, D. R. Fournier, L. Song, T. Piech, P. P. Patel, L. Chang, A. J. Rivnak, E. P. Ferrell, J. D. Randall, G. K. Provuncher, D. R. Walt, D. C. Duffy, Single-molecule enzyme-linked immunosorbent assay detects serum proteins at subfemtomolar concentrations, Nat Biotechnol, 28 (2010) 595-599.

The invention claimed is:

1. A method for the treatment of a myeloid malignancy in a subject, the method comprising administering to the subject a therapeutically effective amount of a lysyl oxidase (LOX) inhibitor, a lysyl oxidase-like (LOXL) inhibitor, or a pharmaceutically acceptable salt thereof or a pharmaceutical composition comprising the inhibitors or salts, wherein the LOX or LOXL inhibitor is

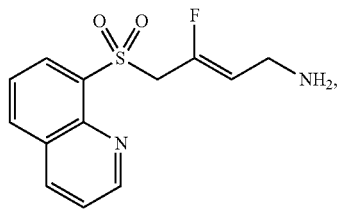 [SMILES: NC/C=C(\F)CS(=O)(=O)c1cccc2cccnc12]

or a pharmaceutically acceptable salt thereof, the method further comprising administering to the subject one or more additional therapeutic agents or a pharmaceutical composition comprising one or more of the additional agents, wherein the additional therapeutic agent is a hypomethylating agent or a pharmaceutically acceptable salt thereof.

2. The method according to claim 1, wherein the myeloid malignancy is selected from the group consisting of myelodysplastic syndromes (MDS), myeloproliferative neoplasms (MPN), MDS/MPS overlap syndromes and acute myeloid leukemia (AML).

3. The method according to claim 2, wherein the AML is acute promyelocytic leukemia (APL).

4. The method according to claim 2, wherein the myeloid malignancy is MDS.

5. The method according to claim 1, wherein the additional therapeutic agent is 5-azacytidine or a pharmaceutically acceptable salt thereof.

6. The method according to claim 5, wherein the myeloid malignancy is MDS.

7. The method according to claim 1, wherein the additional therapeutic agent is decitabine or a pharmaceutically acceptable salt thereof, or a combination of decitabine or a pharmaceutically acceptable salt thereof and a further additional therapeutic agent, the further agent being cedazuridine or a pharmaceutically acceptable salt thereof.

8. The method according to claim 7, wherein the myeloid malignancy is MDS.

9. The method according to claim 7, wherein the combination of the LOX or LOXL inhibitor, or a pharmaceutically acceptable salt thereof, decitabine, or a pharmaceutically acceptable salt thereof, and cedazuridine, or a pharmaceutically acceptable salt thereof, are formulated for oral administration.

* * * * *